United States Patent [19]
Weinshilboum et al.

[11] Patent Number: 5,744,355
[45] Date of Patent: *Apr. 28, 1998

[54] CDNA CLONING AND EXPRESSION OF HUMAN LIVER ESTROGEN SULFOTRANSFERASE

[75] Inventors: Richard M. Weinshilboum; Ibrahim A. Aksoy; Thomas C. Wood, all of Rochester, Minn.

[73] Assignee: Mayo Foundation for Medical Education and Research, Rochester, Minn.

[*] Notice: The portion of the term of this patent subsequent to Oct. 18, 2014, has been disclaimed.

[21] Appl. No.: 437,795

[22] Filed: May 9, 1995

Related U.S. Application Data

[63] Continuation-in-part of Ser. No. 325,562, Oct. 18, 1994.
[51] Int. Cl.$^6$ .............................. C12N 1/21; C12N 5/10; C12N 9/10; C12N 15/54
[52] U.S. Cl. .............. 435/325; 435/193; 435/320.1; 435/252.3; 435/172.3; 536/23.1; 536/23.2
[58] Field of Search ...................... 536/23.1, 23.2; 435/193, 320.1, 252.3, 240.2, 172.3, 325

[56] References Cited

PUBLICATIONS

S.J. Gould et al., Use of the Polymerase Chain Reaction For Homology Probing: Isolation of Partial cDNA of Genomic Clones Encoding the Iron–Sulfur Protein os Succinate Dehydrogenase From Several Species, Proc. Natl. Acad. Sci. 86: 1934–1938, Mar. 1989.
T. Hondoh et al., "Purification and Properties of Estrogen Sulfotransferase of Human Fetal Liver", Biomedical Research 14(2) 129–136, Apr. 1993.
I.A. Aksoy et al., "Cholesterol Sulfation in Human Liver: Catalysis by Dehydroepiandrosterone Sulfotransferase," Drug Metab. Dispos., 21, 268–276 (1993).
I.A. Aksoy et al., "Human liver dehydroepiandrosterone sulfotransferase: Nature and extent of individual variation", Clin. Pharmacol. Ther., 54, 498–506 (1993).
I.A. Askoy, et al., "Human Liver Estrogen Sulfotransferase: Identification by cDNA Cloning and Expression", Biochem. and Biophys. Research Commun. 200 1621–1629 (May 16, 1994).
I.A. Aksoy, et al., "Human Liver Estrogen Sulfotransferase (EST): Polymerase Chain Reaction (PCR) Cloning of cDNA", (Abstract) ISSX Proc., 4 181, 1993.
I.A. Aksoy, et al., "Human Liver Estrogen Sulfotransferase (EST): Polymerase Chain Reaction (PCR) Cloning of cDNA", (Poster Presentation for the Fifth North American Meeting of the International Society for the Study of Xenobiotics) Oct. 18, 1993.
I.A. Aksoy, et al., "Human Estrogen Sulfotransferase. cDNA Cloning, Expression and Characterization", (Abstract), Proc. Amer. Assoc. Cancer Res., 35, 276 (1994).

I.A. Aksoy, et al., "Human Estrogen Sulfotransferase: cDNA Cloning, Expression, and Characterization", (Poster Presentation for the Eighty–Fifth Annual Meeting of the American Association for Cancer Research (AACR)) Apr. 9–13, 1994.
I.A. Aksoy, "Pharmacogenetics of Human Liver Cytosolic Sulfotransferases: Biochemical and Molecular Studies" (May 1994).
R.J. Anderson, et al.,"Phenolsulphotransferase in Human Tissue: Radiochemical Enzymatic Assay and Biochemical Properties," Clin. Chim. Acta., 103, 79–90 (1980).
R.T. Borchardt, et al., "An Ecteola–Cellulose Chromatography Assay for 3'–Phosphoadenosine 5'–Phosphosulfate: Phenol Sulfotransferase," Anal. Biochem., 130, 334–338 (1983).
M.M. Bradford, "A Rapid and Sensitive Method for the Quantitation of Microgram Quantities of Protein Utilizing the Principle of Protein–Dye Binding," Anal. Biochem., 72, 248–254 (1976).
N.R.C. Campbell et al., "Human Liver Phenol Sulfotransferase: Assay Conditions, Biochemical Properties and Partial Purification of Isozymes of the Thermostable Form," Biochem. Pharmacol., 36, 1435–1446 (1987).
W.W. Cleland, "Computer Programmes for Processing Enzyme Kinetic Data," Nature, 198, 463–465 (1963).
W.F. Demyan et al., "Estrogen Sulfotransferase of the Rat Liver: Complementary DNA Cloning and Age– and Sex–Specific Regulation of Messenger RNA," Mol. Endocrinol., 6, 589–597 (1992).
C.N. Falany et al., "Purification and Characterization of Human Liver Dehydroepiandrosterone Sulphotransferase," Biochem. J., 260, pp. 641–646 (1989).
A.A. Farooqui, "3'–Phosphoadenosine 5'–Phosphosulfate Metabolism in Mammalian Tissues," Int. J. Biochem., 12, pp. 529–536 (1980).
A.P. Feinberg et al., "A Technique for Radiolabeling DNA Restriction Endonuclease Fragments to High Specific Activity," Ana. Biochem., 132, 6–13 (1983).
Fiers et al., "Complete nucleodite sequence of SV40 DNA," Nature, 273, 113–120 (1978).
A. Foldes and J.L. Meek, "Rat Brain Phenolsulfotransferase–Partial Purification and Some Properties," Biochem. Biophys. Acta, 327, 365–373 (1973).
K.J. Forbes–Bamforth et al., "Identification of a New Adult Human Liver Sulfotransferase with Specificity for Endogenous and Xenobiotic Estrogens," Biochem. Biophys. Res. Comm., 198, 707–711 (1994).
M.A. Frohman et al., "Rapid Production of Full–Length cDNAs from Rare Transcripts: Amplification Using a Single Gene–Specific Oligonucleotide Primer," Proc. Nat'l. Acad. Sci. USA, 85, 8998–9002 (1988).
F.L. Graham et al., "A New Technique for the Assay of Infectivity of Human Adenovirus 5 DNA," Virology, 52, 456–467 (1973).

Primary Examiner—Rebecca E. Prouty
Attorney, Agent, or Firm—Schwegman, Lundberg, Woessner, & Kluth, P.A.

[57] ABSTRACT

The present invention provides an isolated and purified human DNA molecule that encodes human estrogen sulfotransferase.

8 Claims, 10 Drawing Sheets

F.L. Graham et al., "Characteristics of a Human Cell Line Transformed by DNA from Human Adenvirus Type 5," *J. Gen. Virol.*, 36, 59–72 (1977).

J.S. Hernandez et al., "Sulfation of Estrone and 17β–Estradiol in Human Liver: Catalysis by Thermostable Phenol Sulfotransferase and by Dehydroepiandrosterone Sulfotransferase," *Drug. Metab. Dispos.*, 20, 413–422 (1992).

R. Hobkirk, "Steroid Sulfation: Current Concepts," *Trends Endocrinol. Metab.*, 4, 69–74 (1993).

T. Honkasalo et al., "Determination of Phenol Sulphotransferase Activity by High–Performance Liquid Chromatography," *J. Chromatogr.*, 424, 136–140 (1988).

Hsiao et al., "High–frequency transformation of yeast by plasmids containing the cloned yeast ARG4 gene," *Proc. Natl. Acad. Sci. USA*, 76, 3829–3833 (1979).

W.B. Jakoby et al., "Sulfotransferases" in *Enzymatic Basis of Detoxication;* vol. II, W.B. Jakoby (ed), Academic Press:. New York; pp. 199–229 (1980).

G.A. Johnson et al., "Sulfation of Minoxidil by Liver Sulfotransferase," *Biochem. Pharmacol.*, 31, 2949–2954 (1982).

R.J. Kaufman, "Identification of the Components Necessary for Adenovirus Translational Control and Their Utilization in cDNA Expression Vectors," *Proc. Natl. Acad. Sci. USA*, 82, 689–693 (1985).

Kingsman et al., "Replication in *Saccharomyces cerevisiae* of Plasmid pBR313 Carrying DNA from the Yeast trpl Region," *Gene*, 7, 141–152 (1979).

A–N.T. Kong et al., "Molecular Cloning of the Alcohol/Hydroxysteroid Form ($mST_{a1}$) of Sulfotransferase from Mouse Liver," *Pharmaceut. Res.*, 10, 627–630 (1993).

A–N.T. Kong et al., "Molecular Cloning of cDNA Encoding the Phenol/Aryl Form of Sulfotransferase ($mST_{p1}$) from Mouse Liver," *Biochem. Biophys. Acta*, 1171, 315–318 (1993).

J. Langridge, "Genetic and Enzymatic Experiments Relating to the Tertiary Structure of β–Galactosidase," *J. Bacteriol.*, 96, 1711–1717 (1968).

C.C. Lee et al., "Generation of cDNA Probes Directed by Amino Acid Sequence: Cloning of Urate Oxidase," *Science*, 239, 1288–1291 (1988).

Luckow et al., "Trends in the Development of Baculovirus Expression Vectors," *Bio/Technology*, 6, 47–55 (1988).

H. Luthman et al., "High Efficiency Polyoma DNA Transfection of Chloroquine Treated Cells," *Nucleic Acids Res.*, 11, 1295–1308 (1983).

S. Maeda et al., "Production of Human α–Interferon in Silkworm using a Baculovirus Vector," *Nature*, 315, 592–594 (1985).

M.A. Mancini et al., "Spatio–Temporal Expression of Estrogen Sulfotransferase within the Hepatic Lobule of Male Rats: Implication of in Situ Estrogen Inactivation in Androgen Action," *Endocrinology*, 131, 1541–1546 (1992).

J. Mather et al., "Testicular Cell Culture," *Annals N.Y. Acad. Sci.*, 383, 44–68 (1982).

J. Mather, "Establishment and Characterization of Two Distinct Mouse Testicular Epithelial Cell Lines," *Biol. Reprod.*, 23, 243–252 (1980).

Alan Maxam et al., "Sequencing End–Labeled DNA with Base–Specific Chemical Cleavages," *Methods in Enzymology*, 65, 499–560 (1980).

J. Messing et al., "A System for Shotgun DNA Sequencing," *Nucl. Acids Res.*, 9, 309–321 (1981).

D. Miller et al., "An Insect Baculovirus Host–Vector System for High–Level Expression of Foreign Genes," *Genetic Engineering*, 8, 277–298 (1986).

G.J. Mulder et al., "Sulfation," in *Conjugation Reactions in Drug Metabolism;* Taylor & Francis Ltd.: New York; pp. 107–161 (1990).

R.C. Mulligan et al., "Expression of a Bacterial Gene in Mammalian Cells," *Science*, 209, 1422–1427 (1980).

A.R. Nash et al., "Oestrogen Sulfotransferase: Molecular Cloning and Sequencing of cDNA for Bovine Placental Enzyme," *Aust. J. Biol. Sci.*, 41, 507–516 (1988).

T. Oeda et al., "Molecular Cloning and Expression of a Full–Length Complementary DNA Encoding the Guinea Pig Adrenocortical Estrogen Sulfotransferase," *Mol. Endocrinol.*, 6, 1216–1226 (1992).

D.M. Otterness et al., "Human Liver Dehydroepiandrosterone Sulfotransferase: Molecular Cloning and Expression of cDNA," *Mol. Pharmacol.*, 41, 865–872 (1992).

D.M. Otterness et al., "Human Liver Thermostable Phenol Sulfotransferase: Photoaffinity Labeling with 2–Iodo–4–Azidophenol," *Mol. Pharmacol.*, 36, 856–865 (1989).

G. Pavlakis et al., "Expression of Two Human Growth Hormone Genes in Monkey Cells Infected by Simian Virus 40 Recombinants," *Proc. Natl. Acad. Sci. USA*, 78, 7398–7402 (1981).

R.A. Price et al., "Genetic Polymorphism for Human Platelet Thermostable Phenol Sulfotransferase (TS PST) Activity," *Genetics*, 122, 905–914 (1989).

A. Radiminska et al., "Human Liver Steroid Sulphotransferase Sulphates Bile Acids," *Biochem. J.*, 272, 597–604 (1990).

G. Rein et al., "Multiple Forms of Phenolsulphotransferase in Human Tissues: Selective Inhibition by Dichloronitrophenol," *Biochem. Pharmacol.*, 31, 1893–1897 (1982).

C. Reiter et al., "Thermolabile and Thermostable Human Platelet Phenol Sulfotransferase: Substrate Specificity and Physical Separation," *Naunyn–Schmied. Archiv. Pharmacol.*, 324, 140–147 (1983).

J.I. Rotter et al., "A Genetic Component to the Variation of Dehydroepiandrosterone Sulfate," *Metabolism*, 34, 731–736 (1985).

A.K. Roy, "Regulation of Steroid Hormone Action in Target Cells by Specific Hormone–Inactivating Enzymes," *Proc. Soc. Exp. Biol. Med.*, 199, 265–272 (1992).

R.D. Sekura et al., "Assay of Sulfotransferases," *Analyt. Biochem.*, 95, 82–86 (1979).

F. Stahl et al., "Dehydroepiandrosterone (DHEA) Levels in Patients with Prostatic Cancer, Heart Diseases and Under Surgery Stress," *Exp. Clin. Endocrinol.*, 99, 68–70 (1992).

D.T. Stinchcomb et al., "Isolation and Characterisation of a Yeast Chromosomal Replicator," *Nature*, 282, 39–43 (1979).

R.S. Sundaram et al., "Human Intestinal Phenol Sulfotransferase: Assay Conditions, Activity Levels and Partial Purification of the Thermolabile Form," *Drug Metab. Dispos.*, 17, 255–264 (1989).

G. Tschumper et al., "Sequence of a Yeast DNA Fragment Containing a Chromosomal Replicator and TRP1 Gene," *Gene*, 10, 157–166 (1980).

L. Tseng et al., "Estrogen Sulfotransferase in Human Placenta," *J. Steroid Biochem.*, 22, 611–615 (1985).

G. Urlaub et al., *Proc. Natl. Acad. Sci. USA*, 77, 4216–4220 (1980).

P. Van Solingen et al., "Fusion of Yeast Spheroplasts," *J. Bact., 130,* 946–947 (1977).

L. Varin et al., "Enzymatic Assay for Flavonoid Sulfotransferase," *Anal. Biochem., 161,* 176–180 (1987).

L. Varin et al., "Molecular Characterization of Two Plant Flavonol Sulfotransferase," *Proc. Natl. Acad. Sci. USA, 89,* 1286–1290 (1992).

E. Wahle et al., "The Biochemistry of 3'–End Cleavage and Polyadenylation of Messenger RNA Precursors," *Ann. Rev. Biochem., 61,* 419–440 (1992).

T. Watabe et al., "A 7–hydroxymethyl Sulfate Ester as an Active Metabolite of 7, 12–dimethylbenz[a]anthracene," *Science, 215,* 403–405 (1982).

R.M. Weinshilboum, *Genetic Strategies in Psychobiology and Psychiatry* (E.S. Gershon, S. Matthysse, X.O. Breakefield and R.D. Ciranello, ed.) pp. 79–94; Boxwood Press, Pacific Grove, CA (1981).

R.M. Weinshilboum, "Sulfotransferase Pharmacogenetics," *Pharmacol. Ther., 45,* 93–107 (1990).

R.M. Weinshilboum et al., "Sulfotransferase Enzymes," in *Conjugation–Deconjugation Reactions in Drug Metabolism and Toxicity;* Handbook of Experimental Pharmacology series; F.C. Kauffman, Ed.; Springer–Verlag (1994).

B. Wengle, "Studies on Ester Sulphates. 16. Use of $^{35}$S–labelled Inorganic Sulphate for Quantitative Studies of Sulphate Conjugation in Liver Extracts," *Acta. Chem. Scand., 18,* 65–76 (1964).

R.M. Whittemore et al., "A Modified Ecteola Cellulose Assay for M and P Phenol Sulfotransferase," *Biochem. Pharmacol., 34,* 1647–1652 (1985).

T.W. Wilborn et al., "Sequence Analysis and Expression of the cDNA for the Phenol–Sulfating Form of Human Liver Phenol Sulfotransferase," *Mol. Pharmacol., 43,* 70–77 (1993).

G.N. Wilkinson, "Statistical Estimations in Enzyme Kinetics," *Biochem J., 80,* 324–332 (1961).

G.G. Wong et al., "Human GM–CSF: Molecular Cloning of the Complementary DNA and Purification of the Natural and Recombinant Proteins," *Science, 228,* 810–815 (1985).

T.C. Wood et al., "Human Liver Thermolabile Phenol Sulfotransferase: cDNA Cloning, Expression and Characterization," *Biochem. Biophys. Res. Commun., 198,* 1119–1127 (1994).

HUMAN LIVER EST cDNA

```
-106  AGAAGTGGTTCTCATCTTTTTTTGCAGCTTAAGATCTGCCTTGGTATTTGAAGAGATATA   -47

-46  AACTAGATCAATTTCTTTCACAGGATCAACTAAACAGTGTACCACAATGAATTCTGAACT    14
                                                    M  N  S  E  L

15  TGACTATTATGAAAAGTTTGAAGAAGTCCATGGGATTCTAATGTATAAAGATTTTGTCAA    74
       D  Y  Y  E  K  F  E  E  V  H  G  I  L  M  Y  K  D  F  V  K

75  ATATTGGGATAATGTGGAAGCGTTCCAGGCAAGACCAGATGATCTTGTCATTGCCACCTA   134
       Y  W  D  N  V  E  A  F  Q  A  R  P  D  D  L  V  I  A  T  Y

135  CCCTAAATCTGGTACAACCTGGGTTAGTGAAATTGTGTATATGATCTATAAAGAGGGTGA   194
       P  K  S  G  T  T  W  V  S  E  I  V  Y  M  I  Y  K  E  G  D

195  TGTGGAAAAGTGCAAAGAAGATGTAATTTTTAATCGAATACCTTTCCTGGAATGCAGAAA   254
       V  E  K  C  K  E  D  V  I  F  N  R  I  P  F  L  E  C  R  K

255  AGAAAACCTCATGAATGGAGTAAAACAATTAGATGAGATGAATTCTCCTAGAATTGTGAA   314
       E  N  L  M  N  G  V  K  Q  L  D  E  M  N  S  P  R  I  V  K

315  GACTCATTTGCCACCTGAACTTCTTCCTGCCTCATTTTGGGAAAAGGATTGTAAGATAAT   374
       T  H  L  P  P  E  L  L  P  A  S  F  W  E  K  D  C  K  I  I

375  CTATCTTTGCCGGAATGCAAAGGATGTGGCTGTTTCCTTTTATTATTTCTTTCTAATGGT   434
       Y  L  C  R  N  A  K  D  V  A  V  S  F  Y  Y  F  F  L  M  V

435  GGCTGGTCATCCAAATCCTGGATCCTTTCCAGAGTTTGTGGAGAAATTCATGCAAGGACA   494
       A  G  H  P  N  P  G  S  F  P  E  F  V  E  K  F  M  Q  G  Q

495  GGTTCCTTATGGTTCCTGGTATAAACATGTAAAATCTTGGTGGGAAAAGGGAAAGAGTCC   554
       V  P  Y  G  S  W  Y  K  H  V  K  S  W  W  E  K  G  K  S  P

555  ACGTGTACTATTTCTTTTCTACGAAGACCTGAAAGAGGATATCAGAAAAGAGGTGATAAA   614
       R  V  L  F  L  F  Y  E  D  L  K  E  D  I  R  K  E  V  I  K

615  ATTGATACATTTCCTGGAAAGGAAGCCATCAGAGGAGCTTGTGGACAGGATTATACATCA   674
       L  I  H  F  L  E  R  K  P  S  E  E  L  V  D  R  I  I  H  H

675  TACTTCGTTCCAAGAGATGAAGAACAATCCATCCACAAATTACACAACACTGCCAGACGA   734
       T  S  F  Q  E  M  K  N  N  P  S  T  N  Y  T  T  L  P  D  E

735  AATTATGAACCAGAAATTGTCGCCCTTCATGAGAAAGGGAATTACAGGAGACTGGAAAAA   794
       I  M  N  Q  K  L  S  P  F  M  R  K  G  I  T  G  D  W  K  N

795  TCACTTTACAGTAGCCCTGAATGAAAAATTTGATAAACATTATGAGCAGCAAATGAAGGA   854
       H  F  T  V  A  L  N  E  K  F  D  K  H  Y  E  Q  Q  M  K  E

855  ATCTACACTGAAGTTTCGAACTGAGATCTAAGAAGGTCTTTCTTTACTTAACATATCTGA   914
       S  T  L  K  F  R  T  E  I  *

915  TATTAAAGATTTCTTTTCATTATTCAAAAAAAAAAAAAAAAA                     957
```

FIG. 2

CDNA CLONING AND EXPRESSION OF HUMAN LIVER ESTROGEN SULFOTRANSFERASE

This is a continuation-in-part application of U.S. patent application Ser. No. 08/325,562 filed Oct. 18, 1994, which is incorporated herein by reference.

BACKGROUND OF THE INVENTION

The metabolism of many drugs, xenobiotics, neurotransmitters and hormones includes a step involving the enzymatic addition of a sulfate ($SO_4^{-2}$) group. The addition of a sulfate group is commonly referred to as sulfate conjugation, or simply sulfation. The enzymes responsible for sulfate conjugation are known as sulfotransferases, as they act by transferring a sulfate group from one biological molecule (the sulfate donor) to another (the sulfate acceptor) in a sulfotransferase reaction.

Sulfation is one of the major so-called "Phase II" reactions involved in the inactivation and biotransformation of drugs and xenobiotics. It is also an important metabolic pathway for numerous endogenous molecules. Awareness of the role of sulfation in the metabolism and function of endogenous compounds has increased in recent years. Recognized endogenous substrates for sulfation include steroids, bile acids, catecholamines, tyrosyl residues in proteins and polypeptides and sugar residues in glycoproteins, glycosaminoglycans and glycolipids.

Cytosolic sulfotransferase (ST) enzymes in human liver have been subjected to intensive research. Sulfation increases the water solubility of most compounds and, therefore, their renal excretion. It also usually results in a decrease in biological activity. However, in some cases, sulfate conjugation is required to activate drugs such as the antihypertensive medication minoxidil (G. A. Johnson et al., Biochem. Pharmacol., 31, 2949–2954 (1982)), and it can also play a role in the bioactivation of procarcinogens such as hydroxylarylamines (T. Watabe et al., Science, 215, 403 (1982)).

Human liver tissue is known to catalyze a number of sulfotransferase reactions, all of which utilize 3'-phosphoadenosine-5'-phosphosulfate (PAPS) as a sulfate donor (G. J. Mulder et al., Conjugation Reactions in Drug Metabolism, 107–161, Taylor & Francis Ltd., New York (1990)). Specific cytosolic sulfotransferase enzymes that are present in human liver include dehydroepiandrosterone sulfotransferase (DHEA ST) and two forms of phenol sulfotransferase (PST), known as thermolabile PST (TL PST) and thermostabile PST (TS PST).

These three enzymes can be characterized and classified by their thermostability, their sensitivity to inhibition by 2,6-dichloro-4-nitrophenol (DCNP), a competitive inhibitor of some types of sulfotransferase activity, and by their preferred substrates. DHEA ST catalyzes the sulfate conjugation of cholesterol, bile acids and steroid hormones. It is relatively thermostable and is relatively resistant to DCNP inhibition. TL PST is also relatively resistant to DCNP inhibition but is, as its name indicates, thermolabile. This sulfotransferase preferentially catalyzes the sulfate conjugation of micromolar concentrations of dopamine and other phenolic monoamines. In contrast, TS PST is thermostabile, very sensitive to DCNP inhibition, and catalyzes the sulfation of micromolar concentrations of simple planar phenols such as 4-nitrophenol.

Estrogens are not preferred substrates for any of these three human liver sulfotransferase enzymes. Only two (DHEA ST and TS PST) are even capable of catalyzing the sulfation of estrogens. Sulfotransferase enzymes specific for estrogen (estrogen sulfotransferases, known also as EST enzymes or simply "ESTs") are, however, known for several nonhuman species (A. R. Nash et al., Aust. J. Biol. Sci. 41, 507–516 (1988); W. F. Demyan et al., Mol. Endocrinol., 6, 589–597 (1992); T. Oeda et al., Mol. Endocrinol., 6 1216–1226 (1992)), and show a high degree of sequence homology. Pairwise comparisons between the amino acid sequences of ESTs in rat liver, bovine placenta and guinea pig adrenal cortex show a high level of identity (66–70%). This suggests that mammalian ESTs may be members of a subfamily within a sulfotransferase gene superfamily—a subfamily distinct from those to which the PSTs and DHEA ST belong. It has been suggested that differences in the formation of estrogen sulfates might play a role in variation in response to various estrogens and other structurally-related therapeutic agents (R. Hobkirk, Trends Endocrinol. Metab., 4, 69–74 (1993); A. K. Roy, Proc. Soc. Exp. Biol. Med., 199, 265–272 (1992); M. A. Mancini et al., Endocrinology, 131, 1541–1546 (1992)). It would be a significant medical advance to discover, clone, and characterize complementary DNA (cDNA) encoding a human EST enzyme.

To date, vigorous genetic engineering efforts in the field of sulfate metabolism have resulted in the cloning and expression of cDNAs for several sulfotransferase enzymes: human liver DHEA ST (D. M. Otterness et al., Mol. Pharmacol., 41, 865–872 (1992)), TS PST (W. Wilborn et al., Mol. Pharmacol., 43, 70–77 (1993)), TL PST (T. C. Wood et al., Biochem. Biophys. Res. Commun., 198, 1119–1127 (1994)) and a group of ESTs isolated from several tissues of nonhuman mammalian species (A. R. Nash et al., Aust. J. Biol. Sci., 41, 507–516 (1988); W. F. Demyan et al., Mol. Endocrinol., 6, 589–597 (1992); T. Oeda et al., Mol. Endocrinol., 6, 1216–1226 (1992)). No group has yet identified or cloned a human estrogen sulfotransferase cDNA.

Estrogen sulfotransferase activity (EST activity) has been detected in human liver (K. J. Forbes-Bamforth et al., Biochem. Biophys. Res. Commun., 198, 707–711 (1994). However, a human EST cDNA was not isolated. Identification of a human estrogen sulfotransferase cDNA, and production of human estrogen sulfotransferase enzyme, would be useful in the determination of which endogenous steroid hormones and/or drugs might be metabolized by the protein encoded by the cDNA. Cell lines expressing a human EST enzyme could be constructed from the cloned EST cDNA using methods of genetic engineering known in the art. The resulting availability of recombinant human EST enzyme would be extremely useful to workers in the field of human reproductive metabolism. For example, the expressed human EST enzyme could be used in a laboratory setting to identify other compounds, structurally related to estrogen, that are metabolized by human EST. The affinity of human EST enzyme for these substrates could be directly measured. Potential metabolic pathways of new therapeutic hormones developed by drug companies could be more easily predicted, and potential differences in their pharmokinetic parameters could be anticipated prior to testing in humans. If human EST enzyme were available, experimental use of animals to study the metabolism of newly developed estrogen-like compounds would likely decrease, since animal ESTs will differ in their affinity for such compounds.

Human EST enzyme is undoubtedly an important hormone and drug-metabolizing enzyme. It would be of significant clinical, diagnostic, and therapeutic importance to know which human tissues express an EST, and to have a means of quantifying that expression level. If a human cDNA sequence were known, tissue-specific expression of the human mRNA encoding EST could be investigated using Northern blot analysis. Likewise, tissue-specific EST protein expression could be studied. Identification of a human EST cDNA would lead directly to knowledge of the amino acid sequence encoded thereby. Synthetic antigens derived from this amino acid sequence could be used to obtain anti-EST antibodies useful for immunohistochemical location of EST enzyme in human tissues and for Western blot analysis of the protein expression level of EST in different human tissues. These techniques would not only permit determination of the extent of variation in the expression of EST in humans, but would also make possible the detection of mutations that may alter the ability of EST enzyme to catalyze the metabolism of endogenous hormones or of drugs that are structurally related to endogenous hormones. Therefore, what is needed is a DNA molecule that encodes human estrogen sulfotransferase.

BRIEF DESCRIPTION OF THE FIGURES

FIG. 2. Human liver EST cDNA nucleotide (SEQ ID NO:1) and deduced amino acid sequence (SEQ ID NO:2). Nucleotides are numbered in the 5' to 3' direction with the adenosine of the translation initiation codon designated as +1. The polyadenylation signal sequence ATTAAA is underlined.

SUMMARY OF THE INVENTION

Figure 1:
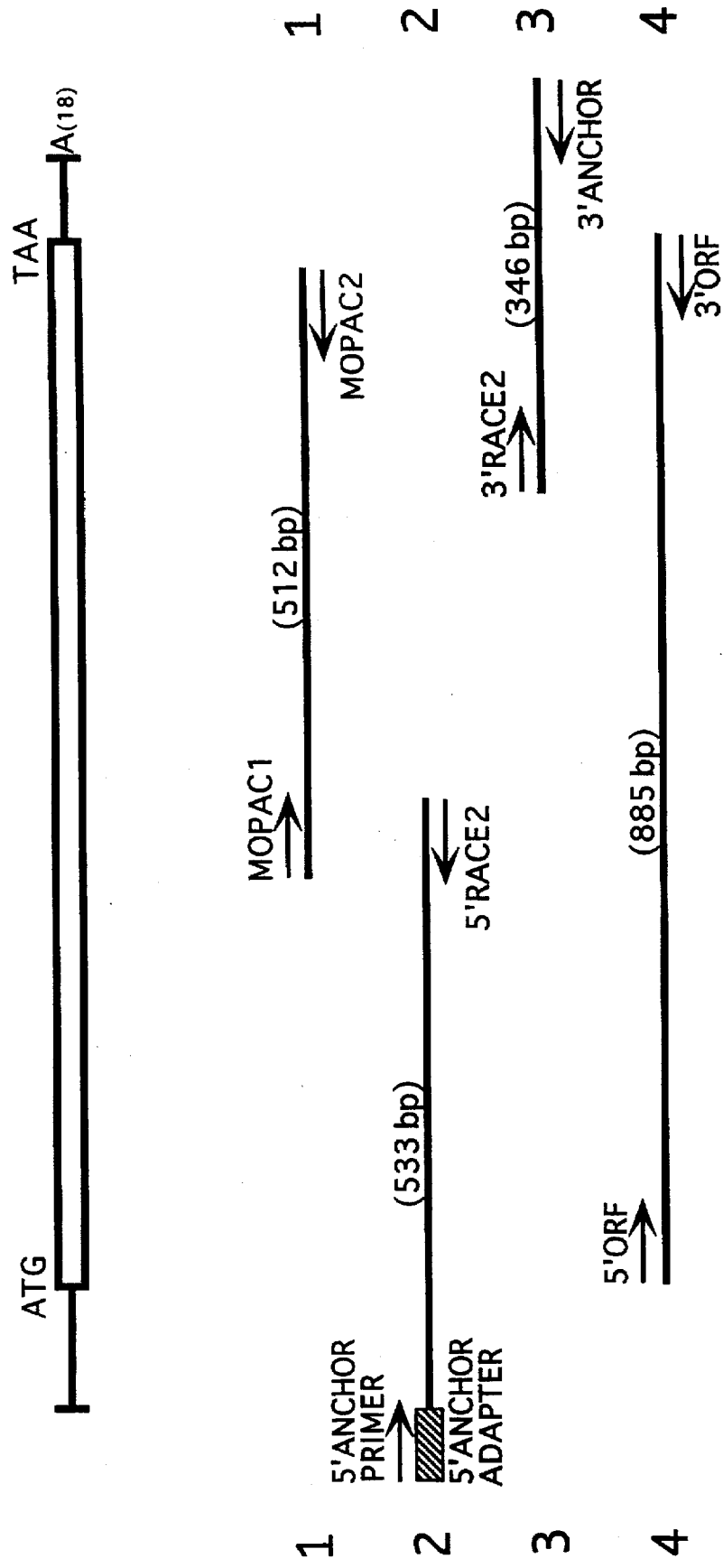
FIG. 1. Cloning strategy for human liver EST cDNA. The full-length human liver EST cDNA is depicted at the top of the diagram in which the box represents the open reading frame (ORF), while solid lines represent the 5'- and 3'-untranslated regions (UTRs). Oligonucleotide primers used in the invention are schematically represented by arrows, and PCR amplification products are schematically represented by the solid lines associated with each primer pair.

The present invention provides an isolated and purified DNA encoding human estrogen sulfotransferase that hybridizes to DNA complementary to DNA having SEQ ID NO:1 under the stringency conditions of hybridization in buffer containing 20% formamide, 5× Denhardt's, 6× SSC, 100 mg/ml RNA and 0.05% sodium pyrophosphate, at 42° C., followed by washing at 60° C. and 1× SSC, 0.1% SDS. Preferably, the present invention provides an isolated and purified DNA encoding the estrogen sulfotransferase having an amino acid sequence which has the amino acide sequence shown in FIG. 2 (SEQ ID NO:2). Preferably, the DNA is cDNA which has the nucleotide sequence shown in FIG. 2 (SEQ ID NO: 1).

DETAILED DESCRIPTION OF THE INVENTION

Specifically, the present invention is directed to the cloning and expression of human estrogen sulfotransferase cDNA as well as the characterization and production of a human estrogen sulfotransferase enzyme (EST). To that end, the invention provides an isolated and purified human DNA encoding a human estrogen sulfotransferase (EST) protein or biologically active derivative thereof. More preferably, the cDNA molecule encodes the protein represented by the amino acid sequence shown in FIG. 2 (SEQ ID NO:2). Most preferably, the cDNA molecule is represented by the complete nucleotide sequence shown in FIG. 2 (SEQ ID NO:1). Isolated and purified peptides encoded by this DNA which are biologically active are also within the scope of the invention.

As used herein, the terms "isolated and purified" refer to in vitro isolation of a DNA molecule or peptide from its natural cellular environment, and from association with other coding regions of the human genome, so that it can be sequenced, replicated, and/or expressed. Preferably, the isolated and purified DNA molecules of the invention comprise a single coding region. Thus, the present DNA molecules are those "consisting essentially of" a DNA segment encoding an estrogen sulfotransferase protein or biologically active derivative thereof. Although the DNA molecule includes a single coding region, it can contain additional nucleotides that do not detrimentally affect the function of the DNA molecule, i.e., the expression of the estrogen sulfotransferase protein or biologically active derivative thereof. For example, the 5' and 3' untranslated regions may contain variable numbers of nucleotides. Preferably, additional nucleotides are outside the single coding region.

The present invention also provides an isolated and purified DNA molecule that encodes human estrogen sulfotransferase protein and that hybridizes to a DNA molecule complementary to the DNA molecule shown in FIG. 2 (SEQ ID NO:1) under high stringency hybridization conditions. As used herein, "high stringency hybridization conditions" refers to hybridization in buffer containing 20% formamide, 5× Denhardt's, 6× SSC, 100 mg/ml RNA, and 0.05% sodium pyrophosphate at 42° C., followed by washing at 60° C., 0.1% sodium dodecyl sulfate (SDS), and 1× SSC (1× SSC contains 0.15M sodium chloride and 0.015M trisodium citrate, pH 7.0).

The present invention also provides an isolated and purified (preferably chemically synthesized) oligonucleotide of at least seven nucleotides (i.e., a primer or a probe preferably containing no more than 300 nucleotides) which hybridizes to the DNA molecules of the present invention, preferably the cDNA molecule shown in FIG. 2, under high stringency hybridization conditions. Oligonucleotide probes and primers are segments of labeled, single-stranded DNA which will hybridize, or noncovalently bind, with complementary single-stranded DNA to be identified. If desired, the probe and primer can be labeled with any suitable label known to those skilled in the art, including radioactive and nonradioactive labels. Typical radioactive labels include $^{32}P$, $^{125}I$, $^{35}S$, and the like. Nonradioactive labels include, for example, ligands such as biotin or digoxigenin as well as enzymes such as phosphatase or peroxidases, or the various chemiluminescers such as luciferin, or fluorescent compounds like fluorescein and its derivatives. The probe or primer may also be labeled at both ends with different types of labels for ease of separation, as, for example, by using an isotopic label at one end and a biotin label at the other end.

As used herein, the terms estrogen sulfotransferase protein, estrogen sulfotransferase enzyme, estrogen sulfotransferase (EST), and EST enzyme, are used interchangeably, and refer to a sulfotransferase enzyme that shows preference for estrone as a sulfation substrate over the other common sulfotransferase substrates, DHEA, 4-nitrophenol, or dopamine. A "biologically active derivative thereof" is a human estrogen sulfotransferase that is modified by amino acid deletion, addition, substitution, or truncation, or that has been chemically derivatized, but that nonetheless utilizes estrogen as its preferred sulfate-acceptor substrate, and sulfates estrone at a higher level than it sulfates DHEA, 4-nitrophenol, or dopamine. For example, it is known in the art that substitutions of aliphatic amino acids such as alanine, valine and isoleucine with other aliphatic amino acids can often be made without altering the structure or function of a protein. Similarly, substitution of aspartic acid for glutamic acid, in regions other than the active site of an enzyme, are likely to have no appreciable affect on protein structure or function. The term "biologically active derivative" is intended to include ESTs as thus modified. The term also includes fragments, variants, analogs or chemical derivatives of human EST enzyme. The term "fragment" is meant to refer to any polypeptide subset of human EST enzyme. Fragments can be prepared by subjecting human EST to the action of any one of a number of commonly available proteases, such as trypsin, chymotrypsin or pepsin, or to chemical cleavage agents, such as cyanogen bromide. The term "variant" is meant to refer to a molecule substantially similar in structure and function to either the entire human EST molecule or to a fragment thereof. A molecule is said to be "substantially similar" to human EST or a fragment thereof if both molecules have substantially similar amino acid sequences, preferably greater than about 80% sequence identity, or if the three-dimensional backbone structures of the molecules are superimposable, regardless of the level of identity between the amino acid sequences. Thus, provided that two molecules possess estrogen sulfotransferase activity, they are considered variants as that term is used herein even if the structure of one of the molecules is not found in the other, or if the sequences of amino acid residues are not identical. The term "analog" is meant to refer to a protein that differs structurally from the wild type enzyme EST, but possesses sulfotransferase activity utilizing estrogen as a preferred substrate.

The present invention also provides a vector comprising an isolated and purified DNA molecule encoding human estrogen sulfotransferase or a biologically active derivative thereof, preferably the sulfotransferase having the amino acid sequence of FIG. 2. Preferably, the vector includes a single estrogen sulfotransferase coding region as well as a second DNA segment operably linked to the coding sequence and capable of directing expression of human estrogen sulfotransferase, such as a promoter region operably linked to the 5' end of the coding DNA sequence. The vector can also include a DNA segment that is a selectable marker gene or a reporter gene.

The present invention also provides a cell line, preferably mammalian, the genome of which has been augmented by chromosomally integrated non-native DNA encoding human estrogen sulfotransferase as herein described.

Several different methods are available for isolating EST cDNA clones. Most approaches begin with the purification of enzyme protein. Purified protein is then subjected to amino acid microsequencing, either directly or after limited cleavage (FIG. 5). The partial amino acid sequence that is obtained can be used to design degenerate oligonucleotide probes or primers for use in the generation of unique, nondegenerate nucleotide sequences by polymerase chain reaction (PCR), sequences that can in turn be used as probes for screening cDNA libraries. Antibodies raised against purified EST may also be used to isolate EST cDNA clones from cDNA expression libraries.

Alternatively, the sequences of cDNAs for ST enzymes related to EST may be used as starting points in a cloning strategy (FIG. 5), so-called "cloning by homology". Another way of utilizing sequence information from different species is to take advantage of shorter areas of high sequence homology among related ST cDNAs from different species and to perform PCR to obtain "species-specific" nondegenerate nucleotide sequences (Example 1). Such a sequence can then be used for cDNA library screening or even for direct PCR-based cDNA cloning.

The identification of a human EST cDNA allows for the ability to determine which endogenous steroid hormones and/or drugs might be metabolized by the protein encoded by the cDNA. Using standard biochemical procedures well-known in the art, oligonucleotide probes can be used to detect and amplify an EST cDNA molecule in a wide variety of biological samples, including, for example, tissue, and cultured cells. For example, Southern or Northern blotting hybridization techniques using labeled probes can be used. Alternatively, PCR techniques can be used. Nucleic acid sequencing of amplified PCR products can be used to detect mutations in the EST cDNA.

Detection of the EST cDNA can involve the use of the polymerase chain reaction sequence amplification method (PCR) using novel primers. The method involves treating extracted DNA to form single-stranded complementary strands, treating the separate complementary strands of DNA with two oligonucleotide primers, extending the primers to form complementary extension products that act as templates for synthesizing the desired nucleic acid molecule; and detecting the amplified molecule.

DNA primer pairs of known sequence positioned 10–300 base pairs apart that are complementary to the plus and minus strands of the DNA to be amplified can be prepared by well known techniques for the synthesis of oligonucleotides. Conveniently, one end of each primer can be extended and modified to create restriction endonuclease sites when the primer is annealed to the target DNA. These restriction sites facilitate the use of the amplified product for cloning at a later date. The PCR reaction mixture can contain the target DNA, the DNA primer pairs, four deoxyribonucleoside triphosphates, $MgCl_2$, DNA polymerase, and conventional buffers. The DNA can be amplified for a number of cycles. It is generally possible to increase the sensitivity of detection by using a multiplicity of cycles, each cycle consisting of a short period of denaturation of the target DNA at an elevated temperature, cooling of the reaction mixture, and polymerization with the DNA polymerase.

Preferred primer pairs include 5'ORF/3' ORF and MoPAC1/MoPAC2 and are shown in FIG. 1. MoPAC1 and MoPAC2 are each doubly degenrate primers, insofar as at two positions in each of them, two different amino are incorporated at those locations (see Table 1). These primers can be used in various combinations or with any other primer that can be designed to hybridize to a portion of DNA such that the amplified product contains all or part of a sequence encoding EST.

Cloning of the open reading frame encoding EST into the appropriate replicable vectors allows expression of the gene product, EST enzyme, and makes the coding region available for further genetic engineering. Expression of EST enzyme or portions thereof, is useful because these gene products can be used as antigens to produce antibodies, as described in more detail below.

1. Isolation of DNA

DNA containing the region encoding EST may be obtained from any cDNA library prepared from tissue believed to possess the EST mRNA and to express it at a detectable level. Preferably, the cDNA library is derived from human liver or fetal tissue. Alternatively, the region encoding EST may be obtained from a genomic DNA library or by in vitro polynucleotide synthesis from the complete nucleotide acid sequence.

Libraries are screened with appropriate probes designed to identify the cDNA of interest. Preferably, for cDNA libraries, suitable probes include oligonucleotides that consist of known or suspected portions of the EST cDNA from the same or different species; and/or complementary or homologous cDNAs or fragments thereof that consist of the same or a similar DNA. For cDNA expression libraries (which express the protein), suitable probes include monoclonal or polyclonal antibodies that recognize and specifically bind to the EST protein. Appropriate probes for screening cDNA libraries include, but are not limited to, oligonucleotides, cDNAs, or fragments thereof that consist of the same or a similar gene. and/or homologous genomic DNAs or fragments thereof. Screening the cDNA library with the selected probe may be accomplished using standard procedures.

Screening cDNA libraries using synthetic oligonucleotides as probes is a preferred method of practicing this invention. The oligonucleotide sequences selected as probes should be of sufficient length and sufficiently unambiguous to minimize false positives. The actual nucleotide sequence (s) of the probe(s) is usually designed based on regions of the EST cDNA that have the least codon redundancy. The oligonucleotides may be degenerate at one or more positions, i.e., two or more different nucleotides may be incorporated into an oligonucleotide at a given position, resulting in multiple synthetic oligonucleotides. The use of degenerate oligonucleotides is of particular importance where a library is screened from a species in which preferential codon usage is not known.

The oligonucleotide can be labeled such that it can be detected upon hybridization to DNA in the library being screened. A preferred method of labeling is to use ATP and polynucleotide kinase to radiolabel the 5' end of the oligonucleotide. However, other methods may be used to label the oligonucleotide, including, but not limited to, biotinylation or enzyme labeling.

Of particular interest is the EST nucleic acid that encodes a full-length mRNA transcript, including the complete coding region for the gene product, EST enzyme. Nucleic acid containing the complete coding region can be obtained by screening selected cDNA libraries using the deduced amino acid sequence.

An alternative means to isolate the DNA encoding EST enzyme is to use PCR methodology. This method requires the use of oligonucleotide primer probes that will hybridize to the DNA encoding EST. Strategies for selection of PCR primer oligonucleotides are described below.

2. Insertion of DNA into Vector

The nucleic acid containing the EST coding region is preferably inserted into a replicable vector for further cloning (amplification of the DNA) or for expression of the gene product, EST enzyme. Many vectors are available, and selection of the appropriate vector will depend on: 1) whether it is to be used for DNA amplification or for DNA expression; 2) the size of the nucleic acid to be inserted into the vector; and 3) the host cell to be transformed with the vector. Most expression vectors are "shuttle" vectors, i.e., they are capable of replication in at least one class of organism but can be transfected into another organism for expression. For example, a vector is cloned in *E. coli* and then the same vector is transfected into yeast or mammalian cells for expression even though it is not capable of replicating independently of the host cell chromosome. Each replicable vector contains various structural components depending on its function (amplification of DNA or expression of DNA) and the host cell with which it is compatible. These components are described in detail below.

Construction of suitable vectors employs standard ligation techniques known in the art. Isolated plasmids or DNA fragments are cleaved, tailored, and relegated in the form desired to generate the plasmids required. Typically, the ligation mixtures are used to transform *E. coli* K12 strain 294 (ATCC 31,446) and successful transformants are selected by ampicillin or tetracycline resistance where appropriate. Plasmids from the transformants are prepared, analyzed by restriction endonuclease digestion, and/or sequenced by methods known in the art. See, e.g., Messing et al., *Nucl. Acids Res.*, 9, 309 (1981) and Maxam et al., *Methods in Enzymology*, 65, 499 (1980).

Replicable cloning and expression vector components generally include, but are not limited to, one or more of the following: a signal sequence, an origin of replication, one or more marker genes, an enhancer element, a promoter and a transcription termination sequence.

Vector component: signal sequence. A signal sequence may be used to facilitate extracellular transport of a cloned protein. To this end, the EST gene product, EST enzyme, may be expressed not only directly, but also as a fusion product with a heterologous polypeptide, preferably a signal sequence or other polypeptide having a specific cleavage site at the N-terminus of the cloned protein or polypeptide. The signal sequence may be a component of the vector, or it may be a part of the EST DNA that is inserted into the vector. The heterologous signal sequence selected should be one that is recognized and processed (i.e., cleaved by a signal peptidase) by the host cell. For prokaryotic host cells, a prokaryotic signal sequence may be selected, for example, from the group of the alkaline phosphatase, penicillinase, 1 pp or heat-stable intertoxin II leaders. For yeast secretion, the signal sequence used may be, for example, the yeast invertase, alpha factor, or acid phosphatase leaders. In mammalian cell expression, a native signal sequence may be satisfactory, although other mammalian signal sequences may be suitable, such as signal sequences from secreted polypeptides of the same or related species, as well as viral secretory leaders, for example, the herpes simplex gD signal.

Vector component: origin of replication. Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast and viruses. The origin of replication from the plasmid pBR322 is suitable for most Gram-negative bacteria, the 2 m plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

Vector component: marker gene. Expression and cloning vectors may contain a marker gene, also termed a selection gene or selectable marker. This gene encodes a protein necessary for the survival or growth of transformed host cells grown in a selective culture medium. Host cells not transformed with the vector containing the selection gene will not survive in the culture medium. Typical selection genes encode proteins that: (a) confer resistance to antibiotics or other toxins, e.g., ampicillin, neomycin, methotrexate, streptomycin or tetracycline; (b) complement auxotrophic deficiencies; or (c) supply critical nutrients not available from complex media, e.g., the gene encoding D-alanine racemase for Bacilli. One example of a selection scheme utilizes a drug to arrest growth of a host cell. Those cells that are successfully transformed with a heterologous gene express a protein conferring drug resistance and thus survive the selection regimen.

An example of suitable selectable markers for mammalian cells are those that enable the identification of cells competent to take up the EST nucleic acid, such as dihydrofolate reductase (DHFR) or thymidine kinase. The mammalian cell transformants are placed under selection pressure that only transformants are uniquely adapted to survive by virtue of having taken up the marker. For example, cells transformed with the DHFR selection gene are first identified by culturing all the transformants in a culture medium that contains methotrexate, a competitive antagonist for DHFR. An appropriate host cell when wild-type DHFR is employed is the Chinese hamster ovary (CHO) cell line deficient in DHFR activity, prepared and propagated as described by Urlaub et al., Proc. Natl. Acad. Sci. USA, 77, 4216 (1980). The transformed cells are then exposed to increased levels of methotrexate. This leads to the synthesis of multiple copies of the DHFR gene, and, concomitantly, multiple copies of the other DNA comprising the expression vectors, such as the EST cDNA. This amplification technique can be used with any otherwise suitable host, e.g., ATCC No. CCL61 CHO-K1, notwithstanding the presence of endogenous DHFR if, for example, a mutant DHFR gene that is highly resistant to methotrexate is employed. Alternatively, host cells (particularly wild-type hosts that contain endogenous DHFR) transformed or co-transformed with EST DNA, wild-type DHFR protein, and another selectable marker such as aminoglycoside 3' phosphotransferase (APH) can be selected by cell growth in a medium containing a selection agent for the selectable marker such as an aminoglycosidic antibiotic, e.g., kanamycin or neomycin. A suitable selection gene for use in yeast is the trp1 gene present in the yeast plasmid YRp7 (Stinchcomb et al., Nature, 282, 39 (1979); Kingsman et al., Gene, 7, 141 (1979); or Tschemper et al., Gene, 10, 157 (1980)). The trp1 gene provides a selection marker for a mutant strain of yeast lacking the ability to grow in tryptophan, for example, ATCC No. 44076 or PEP4-1 (Jones, Genetics, 85, 12 (1977)). The presence of the trp1 lesion in the yeast host cell genome then provides an effective environment for detecting transformation by growth in the absence of tryptophan. Similarly, Leu2 deficient yeast strains (ATCC 20,622 or 38,626) are complemented by known plasmids bearing the Leu2 gene.

Vector component: promoter. Expression and cloning vectors usually contain a promoter that is recognized by the host organism and is operably linked to the EST nucleic acid. Promoters are untranslated sequences located upstream (5') to the start codon of a structural gene (generally within about 100 to 1000 bp) that control the transcription and translation of a particular nucleic acid sequence, such as the EST nucleic acid sequence, to which they are operably linked. Such promoters typically fall into two classes, inducible and constitutive. Inducible promoters are promoters that initiate increased levels of transcription from DNA under their control in response to some change in culture conditions, e.g., the presence or absence of a nutrient or a change in temperature. In contrast, constitutive promoters produce a constant level of transcription of the cloned DNA segment.

At this time, a large number of promoters recognized by a variety of potential host cells are well known in the art. Promoters are removed from their source DNA using a restriction enzyme digestion and inserted into the cloning vector using standard molecular biology techniques. Native or heterologous promoters can be used to direct amplification and/or expression of EST DNA. Heterologous promoters are preferred, as they generally permit greater transcription and higher yields of expressed protein as compared to the native promoter. Well-known promoters suitable for use with prokaryotic hosts include the beta-lactamase and lactose promoter systems, alkaline phosphatase, a tryptophan (trp) promoter system, and hybrid promoters such as the tac promoter. Such promoters can be ligated to EST DNA using linkers or adapters to supply any required restriction sites. Promoters for use in bacterial systems may contain a Shine-Dalgarno sequence for RNA polymerase binding.

Promoter sequences are known for eukaryotes. Virtually all eukaryotic genes have an AT-rich region located approximately 25 to 30 bp upstream from the site where transcription is initiated Another sequence found 70 to 80 bases upstream from the start of transcription of many genes is the CXCAAT region where X may be any nucleotide. At the 3' end of most eukaryotic genes is an AATAAA sequence that may be a signal for addition of the poly A tail to the 3' end of the coding sequence. All these sequences are suitably inserted into eukaryotic expression vectors. Examples of suitable promoting sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase and glucokinase. Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization.

EST transcription from vectors in mammalian host cells can be controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, Hepatitis-B virus and most preferably Simian Virus 40 (SV40) (Fiers et al., *Nature*, 273, 113 (1978); Mulligan et al., *Science*, 209 1422–1427 (1980); Pavlakis et al., *Proc. Natl., Acad. Sci. USA*, 78 7398–7402 (1981)). Heterologous mammalian promoters (e.g., the actin promoter or an immunoglobulin promoter) and heat-shock promoters can also be used, as can the promoter normally associated with the EST sequence itself, provided such promoters are compatible with the host cell systems.

Vector component: enhancer element. Transcription of EST DNA by higher eukaryotes can be increased by inserting an enhancer sequence into the vector. Enhancers are cis-acting elements of DNA, usually having about 10 to 300 bp, that act on a promoter to increase its transcription. Enhancers are relatively orientation- and position-independent, having been found 5' and 3' to the transcription unit, within an intron as well as within the coding sequence itself. Many enhancer sequences are now known from mammalian genes (globin, elastase, albumin, alpha-fetoprotein, and insulin). Typically, however, an enhancer from a eukaryotic cell virus will be used. Examples include the SV40 enhancer on the late side of the replication origin, the cytomegalovirus early promoter enhancer, the polyoma enhancer on the late side of the replication origin, and adenovirus enhancers. The enhancer may be spliced into the vector at a position 5' or 3' to the EST cDNA, but is preferably located at a site 5' of the promoter.

Vector component: transcription termination. Expression vectors used in eukaryotic host cells (yeast, fungi, insect, plant, animal, human or nucleated cells from other multicellular organisms) can also contain sequences necessary for the termination of transcription and for stabilizing the MRNA. Such sequences are commonly available from the 5' and, occasionally, 3' untranslated regions of eukaryotic or viral DNAs or cDNAs. These regions can contain nucleotide segments transcribed as polyadenylated fragments in the untranslated portion of mRNA encoding EST.

Also useful are expression vectors that provide for transient expression in mammalian cells of EST DNA. In general, transient expression involves the use of an expression vector that is able to replicate efficiently in a host cell, such that the host cell accumulates many copies of the expression vector and, in turn, synthesizes high levels of a desired polypeptide encoded by the expression vector. Transient expression systems, comprising a suitable expression vector and a host cell, allow for the convenient positive identification of polypeptides encoded by cloned DNAs, as well as for the rapid screening of such polypeptides for desired biological or physiological properties. Thus, transient expression systems are particularly useful in the invention for purposes of identifying analogs and variants of ataxin-1 that have wild-type or variant biological activity.

The genetically engineered plasmid of the invention can be used to transform a host cell. Typically, eukaryotic host cells are used in the expression system according to the invention, although prokaryotic cells may also be used. Preferably, COS-1 cells are transformed with the genetically engineered plasmid of the invention.

Suitable host cells for cloning or expressing the vectors herein are the prokaryote, yeast, or higher eukaryotic cells described above. Suitable prokaryotes include eubacteria, such as Gram-negative or Gram-positive organisms, for example, *E. coli*, Bacilli such as *B. subtilis*, Pseudomonas species such as *P. aeruginosa*, *Salmonella typhimurium*, or *Serratia marcsecans*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting. Preferably the host cell should secrete minimal amounts of proteolytic enzymes. Alternatively, in vitro methods of cloning, e.g., PCR or other nucleic acid polymerase reactions, are suitable.

In addition to prokaryotes, eukaryotic microbes such as filamentous fungi or yeast are suitable hosts for EST-encoding vectors. *Saccaromyces cerevisiae*, or common baker's yeast, is the most commonly used among lower eukaryotic host microorganisms. However, a number of other genera, species, and strains are commonly available and useful herein, such as Schizosaccaromyces pombe, Kluyveromyces hosts such as, e.g., *K. lactis*, *K. fragilis*, *K. bulgaricus*, *K. thermotolerans*, and *K. marxianus*, yarrowia, Pichia pastoris, Candida, Trichoderma reesia, Neurospora crassa, and filamentous fungi such as, e.g., Neurospora, Penicillium, Tolypocladium, and Aspergillus hosts such as *A. nidulans*.

Suitable host cells for the expression of glycosylated EST are derived from multicellular organisms. Such host cells are capable of complex processing and glycosylation activities. In principle, any higher eukaryotic cell culture is workable, whether from vertebrate or invertebrate culture. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. See, e.g., Luckow et al., *Bio/Technology*, 6, 47–55 (1988); Miller et al., *Genetic Engineering*, 8, 277–279 (1986); and Maeda et al., *Nature*, 315, 592–594 (1985). A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

Vertebrate cells can also be used as hosts. Propagation of vertebrate cells in culture (tissue culture) has become a routine procedure in recent years. Examples of useful mammalian host cell lines are monkey kidney CV1 line transformed by SV40 (CAS-7, ATCC CRL-1651); human embryonic kidney line (293 or 293 cells subcloned for growth in suspension culture, Graham et al., *J. Gen. Virol.*, 36, 59

(1977)); baby hamster kidney cells (BHK, ATCC CCL 10); Chinese hamster ovary cells/-DHFR (CHO, Urlaub and Chasin, *Proc. Natl. Acad. Sci. USA,* 77, 4216 (1980)); mouse sertoli cells (TM4, Mather, Biol Reprod., 23, 243–251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (WI 38, ATCC CCL 75); human liver cells (Hep G2, HB 8065); mouse mammary tumor (MMT 060562, ATCC CCL 51); TRI cells (Mather et al., *Annals N.Y. Acad. Sci.,* 383, 44–68 (1982)); MRC 5 cells; FS4 cells; and a human hepatoma line (Hep G2).

In a preferred embodiment of the invention, the eukaryotic host cell COS-1 is transformed with the eukaryotic expression vector p91023(B), into which a cDNA molecule encoding human estrogen sulfotransferase has been subcloned. The transformed COS-1 host cells of the invention are grown, expression of estrogen sulfotransferase is induced, and the cells are harvested and processed using methods and procedures well-known in the art. This genetically engineered expression system provided by the invention is thus a convenient source of human estrogen sulfotransferase.

4. Transfection and transformation

Host cells are transfected and preferably transformed with the above-described expression or cloning vectors of this invention and cultured in conventional nutrient media modified as appropriate for inducing promoters, selecting transformants, or amplifying the genes encoding the desired sequences.

Transfection refers to the taking up of an expression vector by a host cell whether or not any coding sequence are in fact expressed. Numerous methods of transfection are known to the ordinarily skilled artisan, for example, the calcium phosphate precipitation method and electroporation are commonly used. Successful transfection is generally recognized when any indication of the operation of the vector occurs within the host cell.

Transformation means introducing DNA into an organism so that the DNA is replicable, either as an extrachromosomal element or by chromosomal integrant. Depending on the host cell used, transformation is clone using standard techniques appropriate to such cells. Calcium chloride is generally used for prokaryotes or other cells that contain substantial cell-wall barriers. For mammalian cells without cell walls, the calcium phosphate precipitation method of Graham et al., *Virology,* 52, 456–457 (1978) is preferred. Transformations into yeast are typically carried out according to the method of Van Solingen et al., *J. Bact.,* 130, 946 (1977) and Hsiao et al., *Proc. Natl. Acad. Sci. (USA),* 78 3829 (1979). However, other methods for introducing DNA into cells such as by nuclear injection, electroporation, or protoplast fusion may also be used.

5. Cell Culture

Prokaryotic cells used to produce the EST gene product, EST enzyme, are cultured in suitable media, as described generally in Sambrook et al. The mammalian host cells used to produce the EST gene product may be cultured in a variety of media. Commercially available media such as Hams F10 (Sigma), Minimal Essential Medium (MEM, Sigma), RPMI-1640 (Sigma), and Dulbecco's Modified Eagle's Medium (DMEM, Sigma) are suitable for culturing the host cells. These media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as Gentamycin' drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan. Induction of cells, to cause expression of the EST protein, is accomplished using the procedures required by the particular expression system selected. The host cells referred to in this disclosure encompass in in vitro culture as well as cells that are within a host animal. Cells are harvested, and cell extracts are prepared, using standard laboratory protocols. EST protein can be isolated from cell extracts. Optionally, cell extracts may be assayed directly for EST activity.

Sulfotransferases may be purified using anion exchange chromatography, typically performed with DEAE-cellulose or DEAE Sepharose CL-6B, to separate, at least partially, different ST activities. Other chromatographic techniques that may be used in the purification of ST enzymes include hydroxylapatite and gel filtration, preferably in combination with one or more of a variety of affinity chromatographic columns with varying degrees of specificity for ST enzymes. Affinity columns that may be used include Affi-Gel Blue, ATP-agarose chromatography, heparin-Sepharose, ADP-agarose, PAP-agarose, estradiol-17β-Sepharose, and p-hydroxyphenylacetic acid-agarose. The availability of purified EST enzyme makes it possible to characterize the enzyme and to develop antibodies that can be used, for example, to screen cDNA expression libraries.

EST variants in which residues have been deleted, inserted, or substituted are recovered in the same fashion as native EST enzyme, taking account of any substantial changes in properties occasioned by the variation. For example, preparation of an EST fusion with another protein or polypeptide, e.g., a bacterial or viral antigen, facilitates purification; an immunoaffinity column containing antibody to the antigen can be used to adsorb the fusion polypeptide. Immunoaffinity columns such as a rabbit polyclonal EST column can be employed to absorb the EST variant by binding it to at least one remaining immune epitope. Alternatively, the EST enzyme may be purified by affinity chromatography using a purified EST-IgG coupled to a (preferably) immobilized resin such as Affi-Gel 10 (Bio-Rad, Richmond, Calif.) or the like, by means well-known in the art. A protease inhibitor such as phenyl methyl sulfonyl fluoride (PMSF) also may be useful to inhibit proteolytic degradation during purification, and antibiotics may be included to prevent the growth of adventitious contaminants.

General sulfotransferase activity may be assayed utilizing radioactively-labeled 3'-phosphoadenosine-5'-phosphosulfate (PAPS) (e.g., $^{35}$S-PAPS) or of non-radioactive PAPS with a radioisotope labeled sulfate acceptor substrate. Commonly, a barium precipitation assay is used, in which $^{35}$S-PAPS and $^{35}$SO$_4^{2-}$ are precipitated by barium (A. Foldes et al., *Biochim. Biophys. Acta,* 327 365 (1973); R. J. Anderson et al., *Clin. Chim. Acta,* 103, 79 (1980)). Barium salts of most sulfated reaction products are soluble in water, i.e., they are not precipitated. Specifically, these assays involve incubation of a sulfate acceptor substrate with $^{35}$S-PAPS, followed by termination of the enzymatic reaction by the addition of Ba(OH)$_2$ and ZnSO$_4$. This step is followed by the removal of precipitated $^{35}$S-PAPS by centrifugation, while the radioactively-labeled sulfated product remains in the aqueous phase. Radiactivity in the supernatant is then measured in a liquid scintillation counter. Alternatively, $^{35}$S-PAPS can be separated from sulfated reaction products using thin layer chromatography (R. D. Sekura et al., Anal. Biochem. 95 82 (1979)), Ecteola cellulose chromatographic columns (R. T. Borchardt et al., Anal. Biochem., 130, 334 (1983); R. M. Whittemore et al., Biochem. Pharmacol., 34, 1647 (1985)), high performance liquid chromatography (T. Honkasalo et al., J. Chromatogr., 424, 136 (1988), or organic solvent extraction (L. Varin et al., Anal. Biochem., 161, 176 (1987).

The choice of a "blank" for these assays is critical because of the possibility of the presence of endogenous sulfate acceptor substrates in tissue preparations or even in partially purified enzyme preparations. A sample that does not contain exogenously added sulfate acceptor substrate is typically used as a blank.

Estrogen sulfotransferase activity can be detected and quantified using an enzymatic assay provided by the invention. This assay can be used to measure EST activity in biological samples, preferably human samples, more preferably human liver preparations. The assay is extremely sensitive because it makes use of very highly radioactively labeled $^{35}$S-PAPS; depending upon the expression of the protein in a given tissue, the assay is as sensitive as a radioimmunoassay. It can be used to detect the estrogen sulfotransferase activity of any sulfotransferase enzyme, for example, human EST, DHEA ST and TS PST. The substrate used in the assay can be any estrogen or related chemical compound. Preferably, the substrate is estrone, estradiol-17β, ethinyl estradiol or dehydroepiandrosterone (DHEA). More preferably, estrone is used as the sulfate acceptor substrate in the assay. The assay contains estrone and a magnesium ($Mg^{2+}$) salt in a potassium phosphate buffer at a pH of about 8 to 9. As optimized for assaying human liver extracts, the reaction mixture used in the assay contains 0.3 mM $MgCl_2$, 25 μM estrone, and 50 mM potassium phosphate, pH 8.25. When specifically optimized for assaying EST activity of human EST enzyme expressed in crude extracts from the recombinant EST-P91023(B) COS-1 constructs, described herein, the reaction mixture contains 0.039–10 (preferably 1.25) mM $MgCl_2$, 0.05 μM estrone and 8.2 mM potassium phosphate, pH 5.0–8.9 (preferably 6.5).

Isolation and expression of a cDNA for human liver EST, and the development of an assay for EST activity, represent important steps toward understanding the biotransformation of estrogens in humans. The EST activity assay, while very sensitive, is not, however, specific for the human EST enzyme, since other known sulfotransferases also exhibit varying levels of EST activity. Specific identification of human EST enzyme and quantification of its expression level is nonetheless possible through use of the human EST cDNA provided by the invention. Knowlege of the human EST cDNA sequence leads to knowledge of the EST protein sequence, which in turn makes possible the production of antibodies against portions of the protein sequence specific to human EST protein. Western blot analysis utilizing such antibodies, and Northern analysis using human EST cRNA, are likely to provide highly specific assays for human EST protein expression.

The invention has been described with reference to various specific and preferred embodiments and will be further described by reference to the following detailed examples. It is understood, however, that there are many extensions, variations and modifications on the basic theme of the present invention beyond that shown in the examples and detailed description, which are within the spirit and scope of the present invention.

EXAMPLE I.

PCR-based Cloning of Human Liver EST cDNA

A. Polymerase chain reaction (PCR) using rat EST cDNA as a probe

PCR was used to amplify the open reading frame (ORF) of rat liver EST cDNA. The rat liver PCR amplification product was subcloned, partially sequenced, and used as a probe to screen a human placental and two different human liver cDNA libraries.

Specifically, sense, [5'-GACAGTACACCACTTGTG-3'] (SEQ ID NO: 18), and antisense, [5'-CAGACACA AGGAATTGTC-3'] (SEQ ID NO: 19), primers were designed on the basis of the sequence of rat liver EST cDNA. The PCR was then performed with rat liver first-strand cDNA as template. The resultant amplification product was subcloned into the SmaI site of pBluescript SK+ (Stratagene, La Jolla, Calif.) and was shown to be the rat liver EST cDNA ORF by partial DNA sequencing. The insert was then excised from pBluescript, was radioactivly labeled by random priming with [(α-32P]dCTP (A. P. Feinberg et al., Anal. Biochem., 132, 6 (1983)), and was used as a probe to screen approximately 106 plaques each from human liver and human placental cDNA libraries (Stratagene, La Jolla, Calif.). No positive clones were found.

B. Mixed oligonucleotide primed amplification of cDNA (MOPAC), and PCR using the resulting amplification product as a probe Degenerate primers MOPAC1 and MOPAC2 (Table 1) were designed on the basis of the conserved mammalian amino acid sequences P(A/V)SFWEK (SEQ ID NO:3) and HY(Q/E)QQMK (SEQ ID NO:4). These two amino acid sequences distinguished ESTs from all other known ST amino acid sequences. Only the codons present in bovine, rat and guinea pig ESTs were used to design these MOPAC primers. The GenBank Genetics Sequence Data Bank and the EMBL Nucleotide Sequence Database were used to search for nucleotide homologies, and the Swiss-Prot Protein Database was used to perform protein sequence comparisons.

Total RNA was isolated from a frozen surgical biopsy sample of human liver by extraction with guanidine HCl, followed by centrifugation through a cushion of CsCl. First-strand cDNA was then synthesized with an oligo d(T) primer (Pharmacia, Piscataway, N.J.) and reverse transcriptase (GIBCO BRL, Gaithersburg, Md.). The PCR was then performed in a 100 μl reaction volume (10 mM Tris, pH 8.3; 50 mM KCl; 1.5 mM $MgCl_2$; 0.01% gelatin; 50 μM each of the four deoxynucleoside triphosphates; and 1 unit of Thermus aquaticus DNA polymerase) in a Perkin Elmer Cetus DNA thermal cycler (Emeryville, Calif.) with human liver first strand cDNA as template. The amplification reaction conditions used, after initial denaturation for 10 minutes at 95° C., were 35 cycles of 1 minute at 94° C., 2 minutes at 48° C. and 3 minutes at 72° C., followed by a final 10 minutes incubation at 72° C. A 512 bp amplification product was obtained (FIG. 1). The amplification product was isolated on a 1% agarose gel, removed from the gel with the GeneClean Kit (BIO 101, Inc., La Jolla, Calif.), and its ends were filled in by use of the Klenow fragment of DNA polymerase. This amplification product was subcloned into pBluescript and was sequenced completely on both strands. Specifically, the product was ligated into the SmaI site of pBluescript and transformed into Escherichia coli DH5α made competent by the method of Hanahan (D. Hanahan, J.

*Mol. Biol.,* 166, 557 (1983)). Two positive clones were isolated and partially sequenced by the dideoxy method of Sanger et al. (F. Sanger et al., *Proc. Natl. Acad. Sci. U.S.A.,* 74, 5463 (1977)) with the $^{35}$S-sequencing protocol of the Sequenase kit version 2.0 (United States Biochemical Corp., Cleveland, Ohio). The sequence of the amino acids encoded by the 512 nucleotide insert was 76 to 85% identical to the sequences of bovine, rat and guinea pig EST cDNAs. This 512 bp product, corresponding to a portion of the coding region of a human EST cDNA, was then used to screen human liver, placenta and HepG2 hepatoma cell cDNA libraries, once again without success. Specifically, this 512 nucleotide insert was excised from the plasmid and was radioactively labeled with [α-$^{32}$P]dCTP (A. P. Feinberg, *Anal. Biochem.,* 132, 6 (1983)) with the Oligolabeling Kit (Pharmacia, Piscataway, N.J.). Three different human cDNA libraries, a hepatic cDNA library constructed in the vector Uni-ZAP XR, a HepG2 hepatocarcinoma cell cDNA library also constructed in Uni-ZAP XR, and a placental cDNA library in Lambda ZAPII (Stratagene, La Jolla, Calif.), were screened with the probe, but no positive clones were isolated.

C. Direct PCR cloning of human EST cDNA

Anchored PCR then was performed using the rapid amplification of cDNA ends (RACE) (M. A. Frohman et al., *Proc. Natl. Acad. Sci. USA,* 85, 8998-9002 (1988)) protocol to directly obtain the remaining 5' and 3' terminal portions of human liver EST cDNA. The remaining 5'-portion of human liver EST cDNA was obtained using the EST specific primers 5'-RACE1 and 5'-RACE2 (Table 1 and FIG. 1). The 5'-AmpliFINDER RACE Kit (Clontech, Palo Alto, Calif.) was utilized to synthesize first-strand cDNA from human liver poly(A)+ RNA obtained from Clontech with 5'-RACE1 as a primer, followed by ligation of the 5'-ANCHOR ADAPTER. The PCR was then performed with 5'-RACE2 and 5'-ANCHOR PRIMER to yield an amplification product 533 nucleotides in length (FIG. 1). This product was sequenced with an Applied Biosystems automated DNA sequencer (Foster City, Calif.) in the Mayo Molecular Biology Core Resource Laboratory.

To obtain the 3'-end of the human liver EST cDNA, a 3'-RACE protocol was used with EST specific primers designated 3'-RACE1 and 3'-RACE2 (Table 1). First-strand cDNA synthesis was performed with 2 µg of total human liver RNA as template and the 3'-ANCHOR-d(T)18 primer supplied with the first-strand cDNA Synthesis Kit (Pharmacia, Piscataway, N.J.). The PCR was then performed with this first-strand cDNA as template and 3'-RACE1 and 3'-ANCHOR-d(T) 18 as primers. An amplification product approximately 420 nucleotides in length was obtained, and this product was used as template for a nested PCR performed with 3'-RACE2 and 3'-ANCHOR-d(T)$_{18}$ as primers. The nested PCR yielded an amplification product 346 nucleotides in length (FIG. 1) that was sequenced using the fmol DNA Sequencing System (Promega, Madison, Wis.).

Figure 3A:
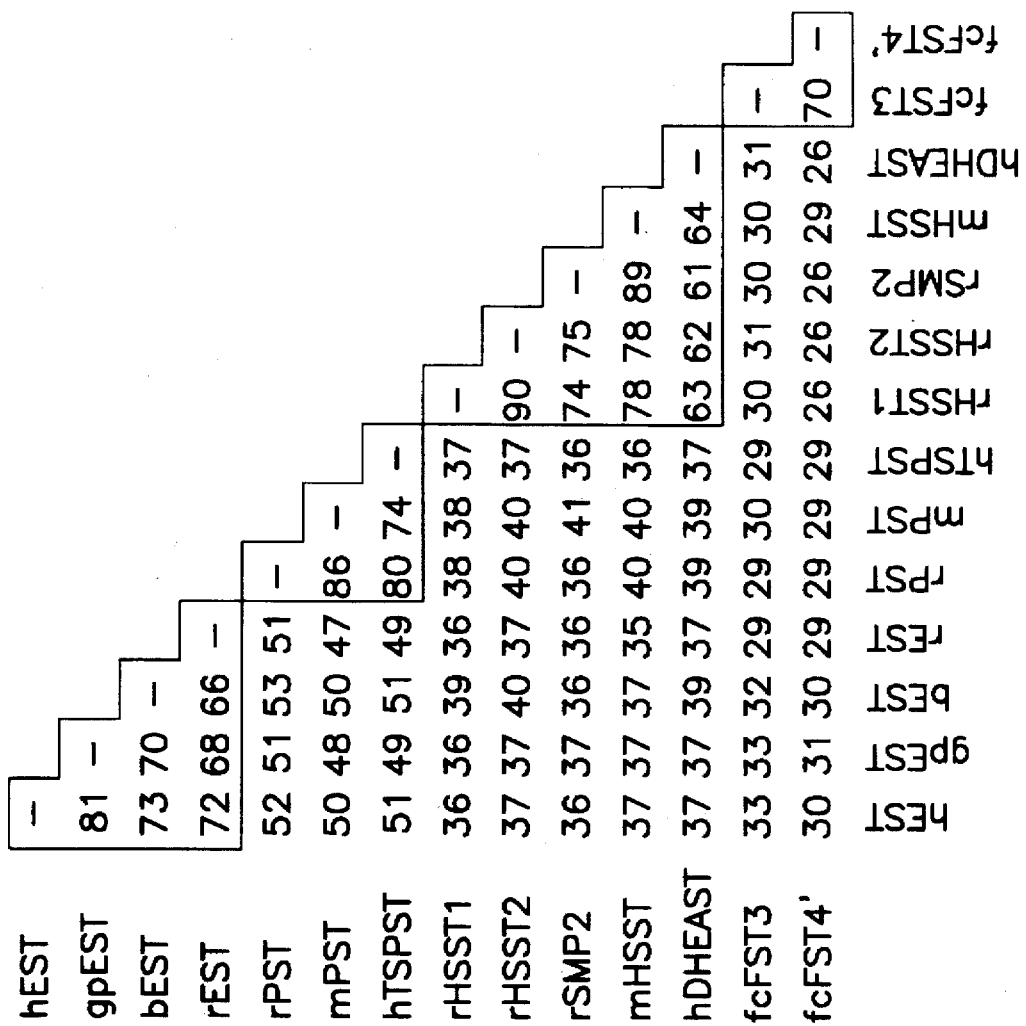
FIG. 3A. Sequence identity among various known cloned sulfotransferases. The enzymes compared include human liver EST (hEST), guinea pig adrenocartical EST (gpEST), bovine placental EST (bEST), rat liver EST (rEST), rat liver PST (rPST), mouse liver PST (mPST), human liver TS PST (hTSPST), rat liver hydroxysteroid ST (rHSST1 and rHSST2), rat liver senescence marker protein 2 (rSMP2), mouse hydroxysteroid (mHSST), human liver DHEA ST (hDHEAST), and *Flaveria chloraefolia* flavonol 3-ST and 4'-ST (fcFST3 and fcFST4'). Values shown represent the percent identity of amino acid sequences as determined by use of the BESTFIT program in the Genetics Computer Group (GCG) package (Madison, Wis.). Boxed values represent comparisons that show greater than 60% sequence identity.
Figure 3B:
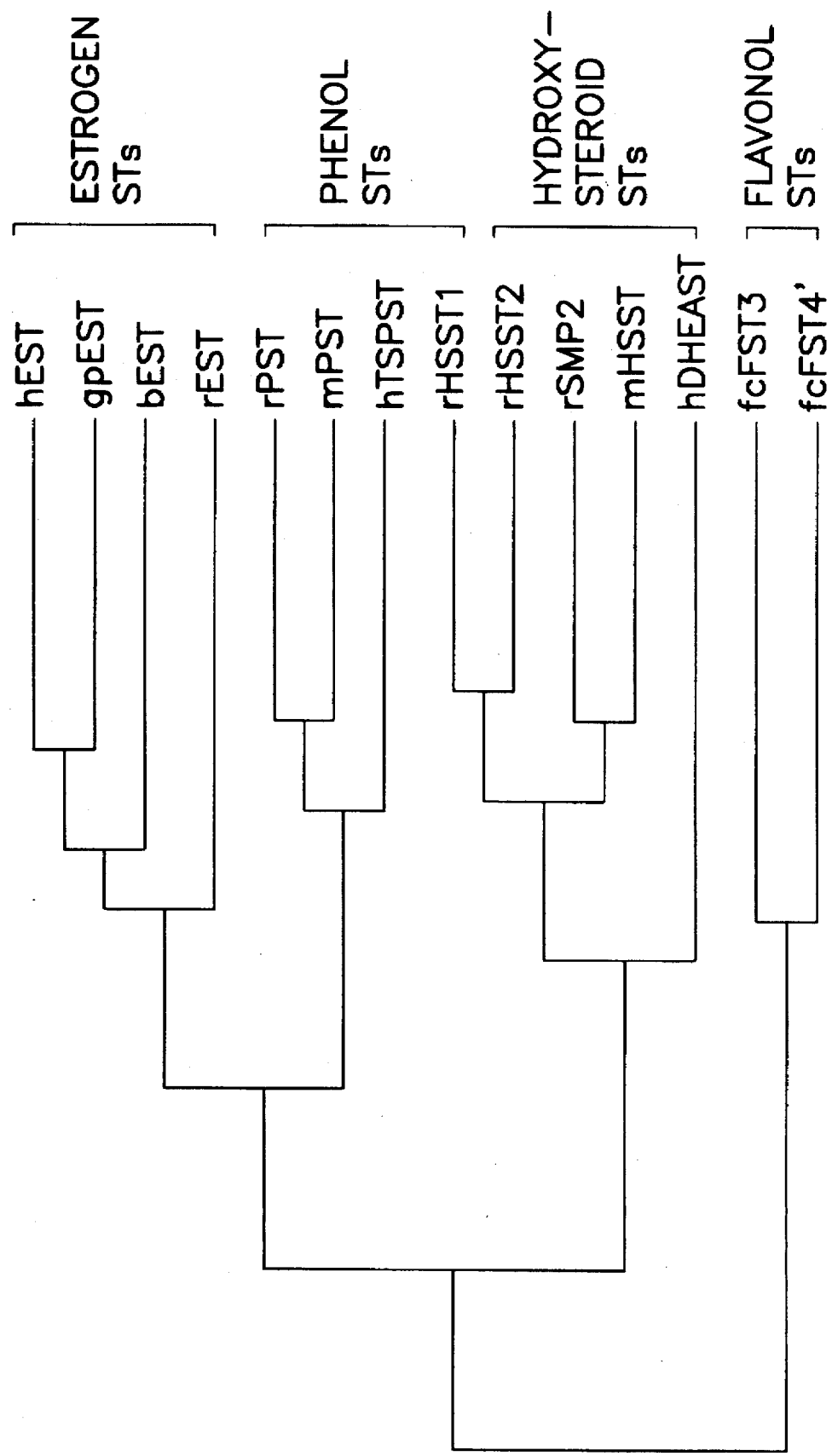
FIG. 3B. Dendogram relating various known cloned sulfotransferases. The functional groupings indicated on the right represent sequences in (FIG. 3A) that were greater than 60% identical. Amino acid sequences were clustered by use of the PILEUP program in the GCG package (Madison, Wis.).

Finally, PCR amplification of the entire EST cDNA coding region (885 bp, FIG. 1) was performed with the primers 5'- and 3'-ORF and with human liver cDNA as template (Table 1, FIG. 1). Specifically, first strand cDNA synthesized from human liver total RNA was used as a template for PCR amplification of the EST cDNA coding region with the primers 5'- and 3'-ORF (Table 1, FIG. 3). An amplification product approximately 920 nucleotide in length was obtained. The 5'- and 3'-end linker MunI restriction sites were digested, and the resulting 885 bp amplification product was subcloned into the EcoRI sites of pBluescript and the eukaryotic expression vector p91023(B) (G. G. Wong et al., *Science,* 228, 810-815 (1985); R. J. Kaufman, *Proc. Natl. Acad. Sci. USA* 82, 689-693 (1985)). The EST-pBluescript construct was used to transform *E. coli* DH5α made competent by the method of Hanahan (D. Hanahan, *J. Mol. Biol.,* 166, 557 (1983)), a positive colony was isolated, and the insert was sequenced completely on both strands. The EST-p91023(B) construct was also used to transform DH5α cells, and positive clones were isolated by colony screening (M. Grunstein et al., *Proc. Natl. Acad. Sci. USA,* 72, 3961 (1975)) performed with the EST cDNA coding region excised from the EST-pBluescript construct and radioactively labeled by random priming with [(α-$^{32}$P] dCTP (A. P. Feinberg et al., *Anal. Biochem.,* 132, 6 (1983)). Orientations of inserts in p91023(B) relative to the promoter were determined by restriction mapping, and one clone with the insert in the sense orientation was sequenced completely on both strands with the $^{35}$S-sequencing protocol of the Sequenase Kit version 2.0 (USB Corp., Cleveland, Ohio). The EST-pBluescript construct was linearized with KpnI, and a T3 RNA transcript was synthesized with the mCAP kit (Stratagene, La Jolla, Calif.).

TABLE 1

Primers used for PCR cloning of human liver EST cDNA. Restriction enzyme recognition sites incorporated into primer sequences are indicated by lines beneath appropriate sequences.

| Primer Designation | Primer Sequence |
|---|---|
| MOPAC1 | 5'-CCAG(C/T)(A/C)TCATTTTGGGAAAA-3' (SEQ ID NO:5) |
| MOPAC2 | 5'-TTCATTTGCTGCT(G/C)(A/G)TAGTG-3' (SEQ ID NO:6) |
| 5'-RACE1 | 5'-CCTGTCCTTGC ATGAATTTCTCCAC-3' (SEQ ID NO:7) |
| 5'-RACE2 | 5'-GATAGATTATCTTACAA-3' (SEQ ID NO:8) |
| 5'-ANCHOR ADAPTER | 5'-CACGAATTCACTATCGATTCTGGAACCTTCAGAGG-3' EcoRI site (SEQ ID NO:9) |
| 5'-ANCHOR PRIMER | 5'-CTGGTTCGGCCCACCTCTGAAGGTTCCAGAATCG ATAG-3' (SEQ ID NO:10) |
| 3'-RACE1 | 5'-GGGAAAGAGTCCACGTGT-3' |

TABLE 1-continued

Primers used for PCR cloning of human liver EST cDNA. Restriction enzyme recognition sites incorporated into primer sequences are indicated by lines beneath appropriate sequences.

| Primer Designation | Primer Sequence |
|---|---|
|  | (SEQ ID NO:11) |
| 3'-RACE2 | 5'-CCATCAGAGGAGCTTGTGGACAGG-3' |
|  | (SEQ ID NO:12) |
| 3'-ANCHOR-d(T)$_{18}$ | 5'-AACTGGAAGAATTCGCGGCCGCAGGAA(T)$_{18}$-3' (SEQ ID NO:13) |
| 5'-ORF | 5'-AGTCCAATTGCAGTGTACCACAATGAATTCTG-3' MunI site (SEQ ID NO:14) |
| 3'-ORF | 5'-GACTCAATTGCCTTCTTAGATCTCAGTTCGAA-3' MunI site (SEQ ID NO:15) |

D. Results.

Initial attempts to detect human EST DNA in human tissue were unsuccessful. First, PCR was used to amplify the entire open reading frame of a rat EST cDNA (subcloned from rat liver DNA). That amplification product was used as a probe to screen human placental and human liver cDNA libraries in an effort to locate a human EST cDNA. No hybridizations were observed, suggesting that a homologous human EST cDNA was not present in these tissues.

Next, a direct PCR-based cloning strategy was adopted that utilized degenerate primers based on highly homologous nucleotide sequences present in the three reported non-human EST cDNAs (A. R. Nash et al., *Aust. J. Biol. Sci.*, 41, 507–516 (1988); W. F. Demyan et al., *Mol. Endocrinol.*, 6, 589–597 (1992); T. Oeda et al., *Mol. Endocrinol.*, 6, 1216–1226 (1992)). This approach has been referred to as "mixed oligonucleotide primed amplification of cDNA" (MOPAC) (C. C. Lee et al., *Science*, 239 1288–1291 (1988)). MOPAC was originally developed to amplify specific DNA sequences by using as primers mixed oligonucleotides designed on the basis of known amino acid sequences. Although no amino acid sequence information was available for human liver EST, it was speculated that adequate sequence homology might exist among ESTs in other species and human liver EST to make it possible to design MOPAC primers. The MOPAC primers were designed on the basis of amino acid sequences that were highly conserved among bovine, rat, and guinea pig ESTs, yet differed from sequences present in other ST enzymes. Based on these "EST-specific" amino acid sequences, two slightly degenerate (4-fold each) oligonucleotide primers (MOPAC1 and MOPAC2, Table 1) were designed. They were used in a PCR with human liver first-strand cDNA as a template. An amplification product 512 nucleotides in length and encoding 170 amino acids (FIG. 1) was obtained. The encoded amino acid sequence was 85, 78 and 76% identical with sequences contained within guinea pig, bovine, and rat ESTs, respectively. This promising 512 bp amplification product was then used to probe human liver, human placental, and human HepG2 hepatoma cell cDNA libraries, but despite the high homology of the 512 bp sequence to other mammalian ESTs, again no hybridization was observed.

Success was finally achieved using a direct PCR-based cloning strategy to obtain the full length human EST cDNA. 5'- and 3'-RACE were used to obtain sequences 5' and 3' to the ends of the 512 bp product. 5'-RACE was employed to obtain the sequence of the remainder of the 5'-end of the coding region as well as the 5'-untranslated region (UTR). The 5'-UTR of the cDNA consisted of 106 nucleotides (FIG. 1). 3'-RACE was used to obtain the sequence of the 3'-end of the ORF as well as the 3'-UTR (Table 1, FIG. 1). The full length human liver EST cDNA consisted of 1063 nucleotides with an 882 nucleotide ORF that encodes 294 amino acids (FIG. 2). The 3'-UTR included 72 nucleotides and ended in a poly(A) tract. The polyadenylation signal ATTAAA was located 24 nucleotides upstream from the poly(A) tract (FIG. 2).

The sequence of the protein encoded by this human liver EST cDNA was 81, 73 and 72% identical with the amino acid sequences of guinea pig adrenocortical, bovine placental, and rat liver ESTs, respectively (FIG. 3A) (A. R. Nash et al., *Aust. J. Biol. Sci.*, 41, 507–516 (1988); W. F. Demyan et al., *Mol. Endocrinol.*, 6, 589–597 (1992); T. Oeda et al., *Mol. Endocrinol.*, 6, 1216–1226 (1992)). However, it was only 37, 51 and 51% identical with the deduced amino acid sequences of human liver DHEA ST, TS PST and TL PST, respectively (FIG. 3A) (D. M. Otterness et al., *Mol. Pharmacol.*, 41, 865–872 (1992); T. W. Wilborn et al., *Mol. Pharmacol.*, 43, 70–77 (1993); T. C. Wood et al., *Biochem. Biophys. Res. Commun.*, 198, 1119–1127 (1994)). Comparison of the deduced amino acid sequence of EST with those of 13 other ST enzymes showed many areas of sequence homology, two of which have been observed to be highly conserved throughout phylogeny. One of those sequences, YPKSGTXW (SEQ ID NO: 16), is located toward the amino, and the other, RKGXXGDWKNXFT (SEQ ID NO: 17), toward the carboxy terminus of the proteins. As used in the amino acid sequences disclosed herein, "X" indicates any amino acid, and the other letters identify specific amino acids in accordance with the standard single-letter code used in the art. Comparisons of percentages of amino acid sequence identities (FIG. 3A) and a dendrogram depicting graphically the relationships among these proteins (FIG. 3B) confirmed that the STs are a gene superfamily with striking sequence identity among orthologous enzymes across species lines.

EXAMPLE II.

Translation and Expression of Human Liver EST cDNA

A. Materials.

[$^{35}$S]PAPS (1.5–2.5 Ci/mmol) was purchased from New England Nuclear (Boston, Mass.). [$\alpha$-$^{32}$P]dCTP (>3000 Ci/mmol) and [$\gamma$-$^{32}$P]ATP (>7000 Ci/mmol) were obtained from ICN Biomedicals, Inc. (Costa Mesa, Calif.). [α-$^{35}$S]-dATP (>1000 Ci/mmol) was purchased from Amersham Corp. (Arlington Heights, Ill.). DNA polymerase, T$_4$ DNA ligase, Moloney murine reverse transcriptase, Dulbecco's modified Eagle's medium (DMEM) and fetal calf serum (FCS) were purchased from GIBCO BRL (Gaithersburg, Md.). Restriction enzymes were obtained from GIBCO BRL, Boehringer Mannheim Corp. (Indianapolis, Ind.) and New England Biolabs (Beverly, Mass.). Estrone, DHEA, dopamine HCl, 4-nitrophenol, DMSO, and chloroquine were purchased from Sigma Chemical Co. (St. Louis, Mo.). DEAE-dextran was obtained from Pharmacia LKB Biotechnology, Inc. (Piscataway, N.J.).

B. In vitro transcription and translation.

In vitro transcription and translation of the 885 bp insert subcloned into pBluescript (Example I) was performed using the TnT® Coupled Reticulocyte Lysate System (Promega Corp., Madison, Wis.). Translation products were analyzed by SDS-PAGE and autoradiography.

C. Expression in COS-1 cells.

COS-1 (ATCC No. CRL-1650) cells were transfected with an EST cDNA expression construct in the eukaryotic expression vector p91023(B) as well as with vector alone using the DEAE-dextran method (H. Luthman et al., *Nucleic Acids Res.*, 11, 1295–1308 (1983)). Specifically, the COS-1 cells were plated in 100-mm dishes in Dulbecco's modified Eagle's medium (DMEM) supplemented with 10% fetal calf serum (FCS) at a density of 1.2×10$^6$ cells/dish, and were grown overnight. The EST-p91023(B) construct, a control human liver DHEA ST-p91023(B) construct, p91023(B) with no insert, or only buffer were mixed with DEAE-dextran and DMEM and were added to the cell culture dishes (J. H. McCutchan et al., *J. Natl. Cancer Inst.*, 41, 351 (1968); R. J. Kaufman et al., *Mol. Cell. Biol.*, 2, 946 (1989)). After 1 hour, the DEAE-dextran solution was replaced for 2 minutes by DMEM that contained 10% dimethylsulfoxide (DMSO), followed by 0.1 mM chloroquine in DMEM for 2 hours (H. Luthman et al., *Nucleic Acids Res.*, 11, 1295 (1983)). Cells were then grown for 48 hours in DMEM supplemented with 10% FCS. After harvesting, cell pellets were washed with 5 ml of phosphate buffered saline (PBS) and were homogenized for 30 seconds in 2 ml of 5 mM potassium phosphate buffer, pH 6.5. The homogenates were centrifuged at 12,000–15,000×g for 15 minutes at 4° C., and supernatants were collected and centrifuged at 100,000×g for 1 hour at 4° C. Five μl aliquots of the 100,000×g "high-speed supernatants" (HSS) were assayed for ST enzymatic activities (Example IV).

D. Results.

The insert subcloned into pBluescript (Example I) contained the entire coding region of the human liver EST cDNA. The major in vitro translation product had an apparent relative molecular weight (M$_r$) of 34.6 kDa as estimated by sodium dodecyl sulfate-polyacrylamide gel electrophoresis (SDS-PAGE). The M$_r$ of recombinant human liver EST enzyme, calculated on the basis of amino acid sequence deduced from the sequence of the cDNA, was 35.1 kDa. ST activities were measured in preparations of transfected COS-1 cells using DHEA, 4-nitrophenol and dopamine, model substrates for DHEA ST, TS PST and TL PST, respectively (Example IV). The assays were performed under optimal conditions for the measurement of these three enzyme activities in human liver preparations (N. R. C. Campbell et al., *Biochem. Pharmacol.*, 36, 1435–1446 (1987); J. S. Hernandez et al., *Drug Metab. Dispos.*, 20, 413–422 (1992), both of which are incorporated herein by reference). The sulfation of estrone was measured using optimal conditions for the assay of EST activity of human EST enzyme (Example III(c)). The protein encoded by the human liver EST cDNA was capable of catalyzing the sulfation of estrone (~9 units/mg protein), DHEA (~2 units/mg protein) and 4-nitrophenol (~5 units/mg protein), but not that of dopamine (Table 2). When transfection was performed with p91023(B) alone or with only buffer, no detectable ST activity was present with any of the substrates tested.

TABLE 2

Expression of ST enzymatic activity after transfection of COS-1 cells with human liver EST cDNA in the eukaryotic expression vector p91023(B). The results of two separate experiments for each substrate are shown.

ST ENZYMATIC ACTIVITY
units/mg protein

| Substrate | No DNA Control | | p91023(B) Control | | EST cDNA | | |
|---|---|---|---|---|---|---|---|
| | Expt. 1 | Expt. 2 | Expt. 1 | Expt. 2 | Expt. 1 | Expt. 1 | Average |
| Estrone | 0.0 | 0.0 | 0.0 | 0.0 | 6.0 | 11.5 | 8.8 |
| DHEA | 0.0 | 0.0 | 0.0 | 0.4 | 1.3 | 3.3 | 2.3 |
| 4-Nitrophenol | 0.0 | 0.0 | 0.0 | 0.0 | 3.4 | 6.9 | 5.2 |
| Dopamine | 0.0 | 0.0 | 0.0 | 0.0 | 0.0 | 0.0 | 0.0 |

EXAMPLE III.

Development of an Estrogen Sulfotransferase Activity Assay

A. Optimized Estrogen Sulfotransferase Activity Assay for Human Liver Preparations.

The ability of the sulfotransferases present in human liver to catalyze the sulfation of estrone (i.e., the EST activity of the sulfotransferases) was assayed using a dilute sample of HSS (high speed supernatent) obtained from crude human liver extracts. Pre-diluted HSS was first made by diluting 50 μl HSS into 450 μl dilution buffer (dilution buffer: 5 mM potassium phosphate, pH 6.5, containing 1.5 mg/ml bovine serum albumin and 1.54 mg/ml dithiothreitol). Diluted HSS was then prepared by diluting 210 μl of the pre-diluted HSS into 6790 μl of dilution buffer, such that 100 μl dilute HSS=0.3 μl HSS, and kept on ice; assays used a 100 μl aliquot of diluted HSS. Concentrated estrone substrate solution was prepared by dissolving estrone in dimethylsulfoxide (DMSO) (0.215 mg estrone/ml DMSO). Concentrated MgCl$_2$.6H$_2$O solution (1.95 mg MgCl$_2$.6H$_2$O/ml H$_2$O) and concentrated DTT solution (7.4 mg/mL H$_2$O) were prepared for use in the optimized EST assay.

The optimized EST assay was performed in 10×75 mm glass culture tubes and was performed in triplicate (controls were performed in duplicate). Total reaction assay volume was about 200 µl. Five µl concentrated $MgCl_2.6H_2O$ solution (for a final reaction concentration of 0.3 mM $MgCl_2.6H_2O$) was placed in each culture tube. Five µl DMSO was then added to the control tubes, whereas 5 µl of the estrone substrate solution (for a final reaction concentration of 25 µM estrone was added to the active tubes. Tubes were placed in ice water and 100 µl dilute HSS was added to each. The enzyme reaction was initiated by adding a ~50 µl "cocktail" containing: 25 µl 50 mM potassium phosphate buffer, pH 11.5, 25 µl concentrated DTT solution, and a sufficient number of µl $^{35}$S-PAPS (determined for each batch of $^{35}$S-PAPS) such that the final reaction concentration was 0.4 µM $^{35}$S-PAPS. The tubes were vortexed, incubated 20 minutes at 37° C. The final pH of the reaction mixture was pH 8.25. The reaction was terminated by the addition of 100 µl "barium mixture" (barium mixture: 1:1 0.1M barium acetate and 0.1M barium hydroxide) followed by addition of 50 µl 0.1M $ZnSO_4$. After centrifugation, 50 µl 0.1M $Ba(OH)_2$ and 50 µl 0.1M $ZnSO_4$ were added to each tube, followed by the addition of 400 µl distilled water. The tubes were vortexed after each addition. After centrifugation, 0.5 ml supernatent was aspirated and combined with 5 mL Bio-Safe II scintillation cocktail in 6 ml scintillation vials, and the mixture was shaken. $^{35}$S radioactivity was measured using a liquid scintillation counter.

B. Identification of the Preferred Substrate for Recombinant Human EST Enzyme.

The recombinant protein encoded by the EST cDNA expressed in the COS-1 construct appeared to have greater sulfotransferase activity when estrone was the sulfate acceptor substrate than was the case with estradiol-17β, ethinyl estradiol, or DHEA.

C. Optimized Estrogen Sulfotransferase Activity Assay for Human Recombinant EST Enzyme.

Estrone was used as the substrate to determine optimal assay conditions and, subsequently, to characterize the properties of human EST enzyme. A range of estrone concentrations from 0.01 to 0.10 µM was tested, and 0.05 µM gave maximal enzymatic activity. The optimal pH for the measurement of estrone ST activity with the expressed protein was approximately 6.5 in the presence of 8.2 mM potassium phosphate buffer. $Mg^{2+}$ is known to increase the activities of several ST enzymes (J. S. Hernández et al., *Drug Metab. Dispos.*, 20, 413–422 (1992); I. A. Aksoy et al., *Druc, Metab. Dispos.*, 21, 268–276 (1993)). Therefore, a range of $Mg^{2+}$ concentrations from 0.04 to 10 mM was tested, and 1.25 mM $Mg^{2+}$ was found to increase EST activity 20% with estrone as a substrate. EST activity assays were subsequently performed on crude extracts from recombinant COS-1 cells expressing human EST enzyme using the optimal assay conditions thus identified: at a reaction pH of 6.5 in the presence of 1.25 mM $MgCl_2$ with 0.05 µM estrone as the sulfate acceptor substrate, in 8.2 mM potassium phosphate buffer.

EXAMPLE IV.

Biochemical Characterization of Recombinant Human EST Enzyme and Comparison with Recombinant DHEA ST Enzyme Biochemical characterization of recombinant human EST enzyme were carried out using aliquots of HSS from COS-1 cells transfected with human liver EST cDNA. Parallel experiments were performed with human liver DHEA ST cDNA (D. M. Otterness et al., *Mol. Pharmacol.*, 41, 865–872 (1992)) that had also been transiently expressed in COS-1 cells.

A. Sulfotransferase (ST) activity.

The ability of human EST enzyme to catalyze sulfation of various substrates was compared. ST activities were assayed by the method of Foldes et al. (*Biochim. Biophys. Acta*, 327, 365–374 (1973)), as modified by Hernández et al. (*Drug Metab. Dispos.* 20, 413–422 (1992)) for the measurement of human liver DHEA ST activity with its preferred substrate, DHEA (Sigma Chemical Co., St. Louis, Mo.), and by Campbell et al. (*Biochem. Pharmacol.*, 36, 1435–1446 (1987)), for the measurement of human liver TS and TL PST activities with their preferred substrates, 4-nitrophenol and dopamine, respectively (Sigma Chemical Co., St. Louis, Mo.). These assays were performed on high-speed supernatants (HSS) of crude COS-1 cell extracts under optimal conditions for the measurement of ST enzyme activities in human liver preparations as described in N. R. C. Campbell et al. (*Biochem. Pharmacol.*, 36, 1435–1446 (1987)) and J. S. Hernández et al. (*Drug Metab. Dispos.*, 20, 413–422 (1992)), both of which are incorporated herein by reference. For the measurement of estrone sulfating activity, the optimized assay conditions for human EST enzymes described in Example III(c) were used. Specifically, the sulfate acceptor substrates used in the various assays were DHEA (5 µM), 4-nitrophenol (4 µM), dopamine (60 µM), and estrone (0.05 µM), respectively. Controls did not contain sulfate acceptor substrates. 1. DHEA ST activity of human EST enzyme.

The ability of human EST enzyme to catalyze the sulfation of DHEA was assayed using a dilute sample of HSS (high speed supernatent). Dilute HSS was made by diluting 50 µl HSS into 9950 µl of dilution buffer, such that 100 µl dilute HSS=0.5 µl HSS (dilution buffer: 5 mM potassium phosphate, pH 6.5, containing 1.5 mg/ml bovine serum albumin and 1.54 mg/ml dithiothreitol) and kept on ice; assays used a 100 µl aliquot of diluted HSS. Concentrated DHEA substrate solution was prepared by dissolving DHEA in dimethylsulfoxide (DMSO) (10× solution: 0.467 mg DHEA/ml DMSO). A 1× solution was prepared by diluting 100 µl of 10× DHEA substrate solution into 900 µl DMSO. Concentrated $MgCl_2.6H_2O$ solution (1.95 mg $MgCl_2.6H_2O$ /ml $H_2O$) and concentrated DTT solution (7.4 mg/mL $H_2O$) were prepared for use in the assay.

The assay was performed in 10×75 mm glass culture tubes and was performed in triplicate (controls were performed in duplicate). Total reaction assay volume was about 200 µl. Five µl concentrated $MgCl_2.6H_2O$ solution (for a final reaction concentration of 0.3 mM $MgCl_2.6H_2O$) was placed in each culture tube. Five µl DMSO was then added to the control tubes, whereas 5 µl of the 1× DHEA substrate solution (for a final reaction concentration of 5 µM DHEA) was added to the active tubes. Tubes were placed in ice water and 100 µl dilute HSS was added to each. The enzyme reaction was initiated by adding a ~50 µl "cocktail" containing: 25 µl 50 mM potassium phosphate buffer, pH 5.5, 25 µl concentrated DTT solution, and a sufficient number of µl $^{35}$S-PAPS (determined for each batch of $^{35}$S-PAPS) such that the final reaction concentration was 0.4 µM $^{35}$S-PAPS. The tubes were vortexed, incubated 20 minutes at 37° C. The final pH of the reaction mixture was pH 6.0. The reaction was terminated by the addition of 100 µl "barium mixture" (barium mixture: 1:1 0.1M barium acetate and 0.1M barium hydroxide) followed by addition of 50 µl 1 0.1M $ZnSO_4$. After centrifugation, 50 µl 1 0.1M $Ba(OH)_2$ and 50 µl 0.1M $ZnSO_4$ were added to each tube, followed by the addition of 400 µl distilled water. The tubes were vortexed after each addition. After centrifugation, 0.5 ml supernatent was aspirated and combined with 5 mL Bio-Safe II scintillation cocktail in 6 ml scintillation vials, and the mixture was shaken. $^{35}$S radioactivity was measured using a liquid scintillation counter.

2. TS PST activity of human EST enzyme.

The ability of human EST enzyme to catalyze the sulfation of 4-nitrophenol was assayed using a more dilute sample of HSS. The dilution buffer described above was used to dilute HSS such that 100 µl dilute HSS=0.015 µl HSS. The assay was carried out substantially as described for the DHEA ST assay above, with the following exceptions. In place of DHEA, 5 µl of a concentrated 4-nitrophenol solution was used as a substrate, such that the final reaction concentration was 4 µM 4-nitrophenol. Water, instead of DMSO, was used in the control tubes. Magnesium (MgCl$_2$.6H$_2$O) was omitted. The pH of the potassium phosphate buffer used in the "cocktail" was pH 6.5, and the final reaction pH was also pH 6.5.

3. TL PST activity of human EST enzyme.

The ability of human EST enzyme to catalyze the sulfation of dopamine was also assayed using a dilute sample of HSS. In this case, the dilution buffer described above was used to dilute HSS such that 100 µl dilute HSS=0.1 µl HSS. The assay was carried out substantially as described for the TS PST assay above, with the following exceptions. Five µl of a concentrated solution of pargyline (1 mM final reaction concentration) was added to all tubes prior to the addition of dopamine. In place of 4-nitrophenol, 5 µl of a concentrated dopamine solution was used as a substrate, such that the final reaction concentration was 60 µM dopamine.

4. EST activity of human EST enzyme.

This assay was performed as described in Example III(c).

For all sulfotransferase assays, one unit of enzyme activity represented the formation of 1 nmol of sulfated product per hour of incubation at 37° C. All assays were performed in triplicate, and values reported in Table 2 are averages of those three determinations. Protein concentrations were measured by the method of Bradford (*Anal. Biochem.*, 72, 248–254 (1976)) with bovine serum albumin as a standard.

B. Kinetics of ST activity.

Substrate kinetic studies designed to estimate apparent $K_m$ values were performed utilizing the EST and DHEA ST activity assays described above and in Example III. Since human liver EST enzyme and DHEA ST enzyme can both catalyze the sulfation of steroids, these studies presented an opportunity to determine apparent $K_m$ values of the two enzymes with estrone and DHEA as substrates. Both enzyme preparations were tested with a range of estrone and DHEA concentrations (Table III).

TABLE 3

|  | COS-1 Expressed EST Enzyme | COS-1 Expressed DHEA ST Enzyme |
|---|---|---|
| [Estrone], (µM) | Range (n = 10) 0.01 to 0.1<br>$K_m = 0.17$ | Range (n = 1) 0.2 to 100<br>$K_m = 3.1$ |
| [DHEA], (µM) | Range (n = 9) 0.0125 to 32<br>$K_m = 0.85$ | Range (n = 11) 0.06 to 10<br>$K_m = 2.6$ |

Apparent $K_m$ values for the sulfation of estrone and DHEA catalyzed by recombinant human liver EST enzyme calculated from these data were 0.17 and 0.85 µM, respectively, while those for reactions catalyzed by recombinant human liver DHEA ST enzyme were 3.1 and 2.6 µM, respectively. Apparent $K_m$ values were calculated by the method of Wilkinson (*Biochem. J.*, 80, 324–332 (1961)) with a computer program written by Cleland (*Nature*, 198, 463–465 (1963)).

C. Thermal inactivation of ST activity.

Figure 4A:
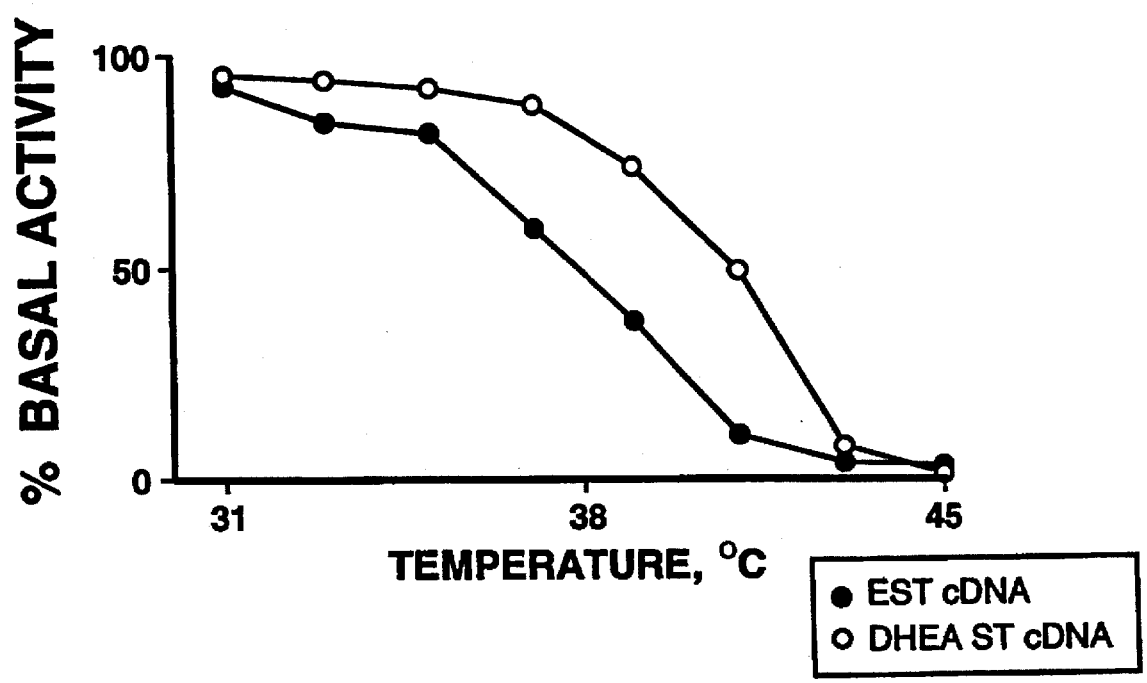
FIGS. 4A–4C. Response of recombinant human liver EST enzyme (closed circles) and recombinant human liver DHEA ST enzyme (open circles) cDNAs expressed in COS-1 cells to changes in (A) temperature; (B) DCNP concentration (using optimized EST and DHEA ST activity assays, respectively); and (C) NaCl concentration (using optimized EST and DHEA ST activity assays, respectively). Each point is the mean of three determinations.

Thermal stability is a sensitive indicator of differences in protein structure and the thermal stabilities of the three well-characterized STs present in the human liver differ dramatically (R. M. Weinshilboum et al., *Conjugation-Deconiugation Reactions in Drug Metabolism and Toxicity*, "Handbook of Experimental Pharmacology" series, R. C. Kauffman, Ed., Springer-Verlag (1994)). Aliquots of recombinant COS-1 cell extracts were incubated at 31°, 33°, 35°, 37°, 39°, 41°, 43° or 45° C. for 15 minutes prior to assay to determine thermal inactivation parameters. The temperatures at which 50% inactivation of EST enzyme (using its preferred substrate, estrone) and DHEA ST enzyme (using its preferred substrate, DHEA) activities occured were 38.2±0.12 (mean ±SEM) and 41.1°±0.10° C., respectively (FIG. 4A). For the thermal inactivation experiment, aliquots of HSS from COS-1 cells transfected with EST cDNA or DHEA ST cDNA were diluted 1:2 (v/v) with 5 mM potassium phosphate buffer, pH 6.5, preincubated at various temperatures for 15 minutes and and was then placed on ice. An aliquot of the same preparation was kept on ice as a control. Each aliquot was then diluted further for assay of the ST activity being measured. Values for controls were determined at each temperature studied. Data obtained during thermal inactivation and DCNP inhibition studies were analyzed with the GraphPAD InPlot curve-fitting program (GraphPAD InPlot Software, San Diego, Calif.). The results are reported in FIG. 4A.

D. DCNP inhibition of EST activity.

Figure 4B:
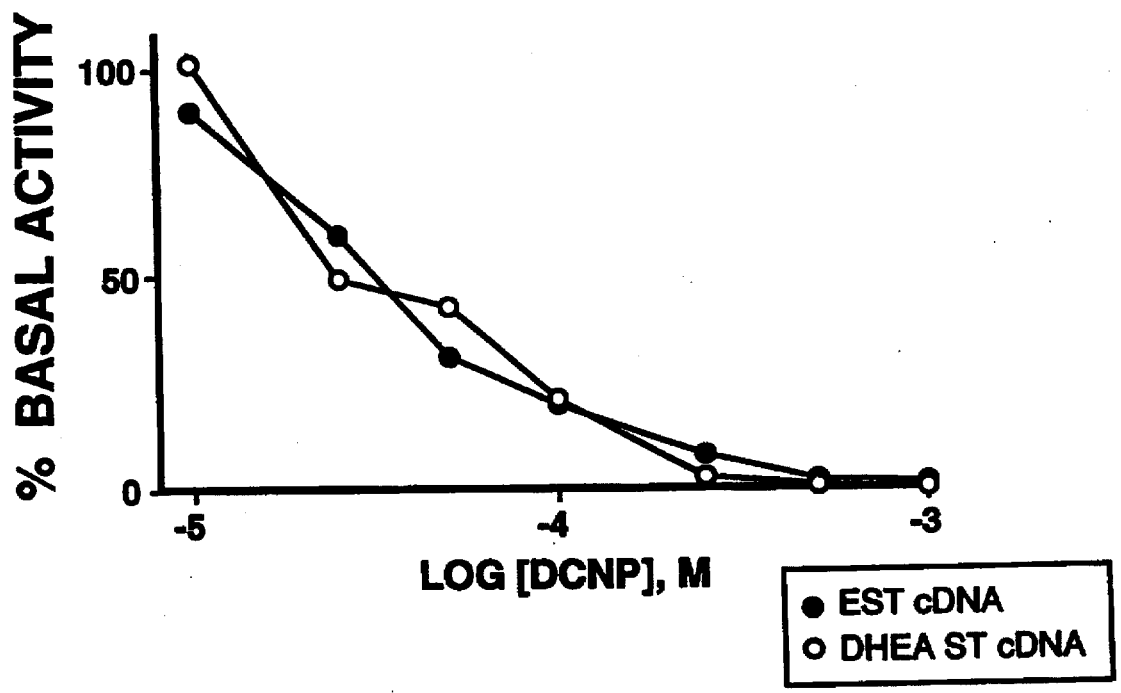

DCNP is a competitive inhibitor of ST enzymes (G. Rein et al., *Biochem. Pharmacol.*, 31, 1893–1897 (1982)), and DCNP inhibition profiles of human liver ST enzymes can differ greatly (R. M. Weinshilboum et al., *Conjugation-Deconiugation Reactions in Drug Metabolism and Toxicity*, "Handbook of Experimental Pharmacology" series, R. C. Kauffman, Ed., Springer-Verlag (1994)). DCNP inactivation was studied for recombinant EST enzyme using the EST activity assay (Example III(c)) and for recombinant DHEA ST enzyme using the DHEA ST activity assay (Example IV(a)) as described. Five µL of concentrated DCNP solution in DMSO was added to a reaction mixture prior to incubation, to give a final reaction concentration of 0.001 to 10 mM DCNP. EST activity of recombinant human liver EST enzyme (using its preferred substrate, estrone) and DHEA ST activity of recombinant human liver DHEA ST enzyme (using its preferred substrate, DHEA) of recombinant human EST enzyme were found to be 50% inhibited at very similar mean DCNP concentrations, 28±2.9 and 40±2.3 µM, respectively (FIG. 4B).

E. Effect of NaCl concentration on EST activity.

Figure 4C:
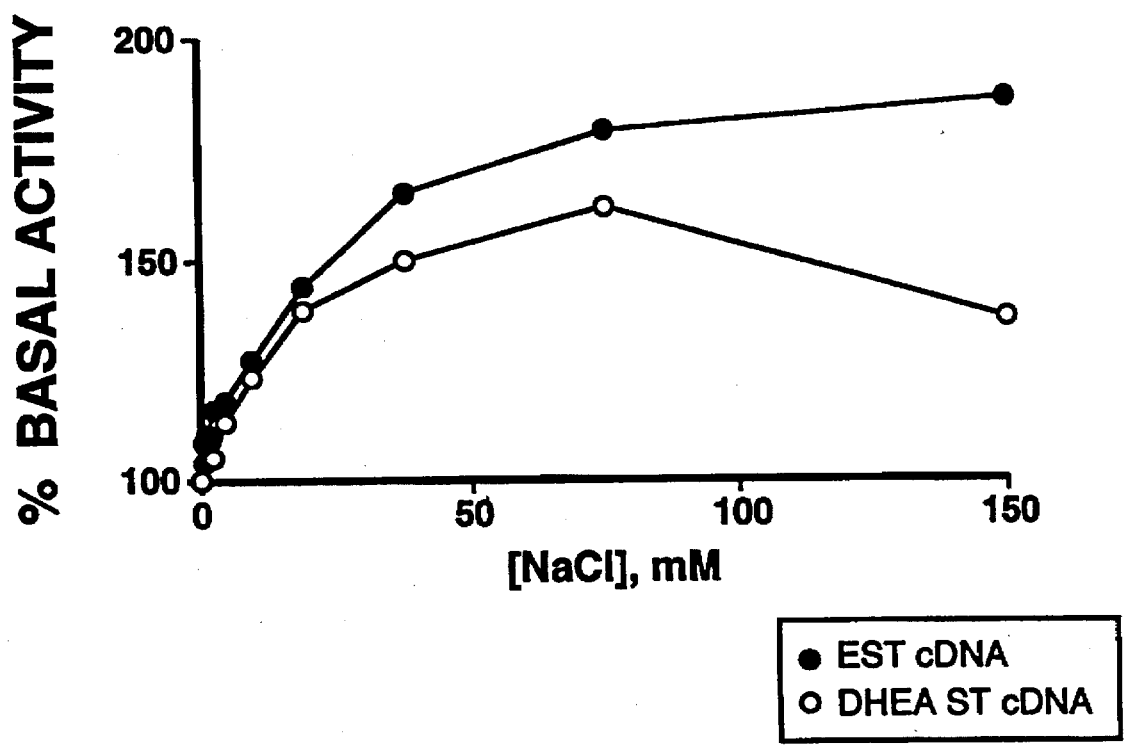
Figure 5A:
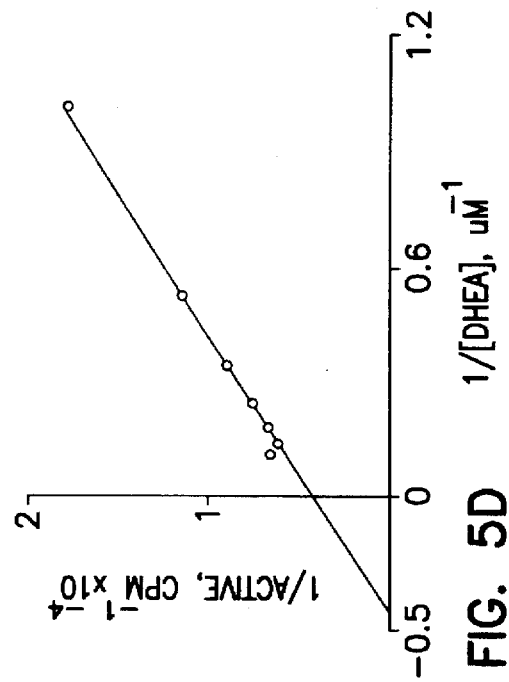
FIGS. 5A–5D. Effect of substrate concentration on the activities of human liver EST and DHEA ST cDNAs expressed in COS-1 cells. Double inverse plots are shown for data obtained with estrone and DHEA as substrates for EST cDNA (A and B) and for DHEA ST cDNA (C and D) expressed in COS-1 cells. Each point is the mean of three determinations.
Figure 5B:
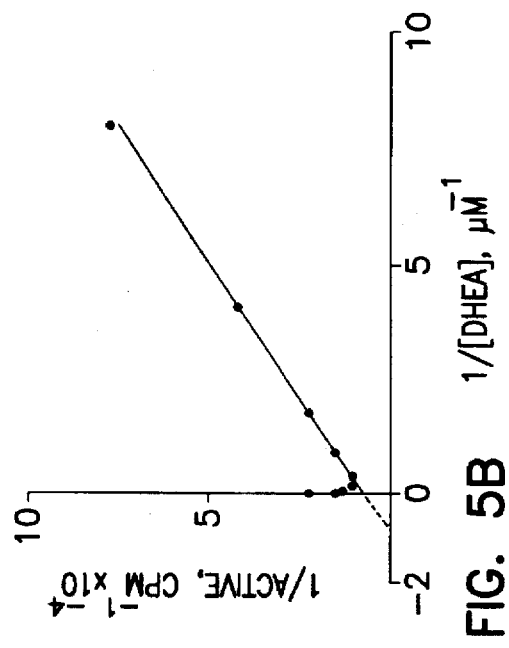
Figure 5C:
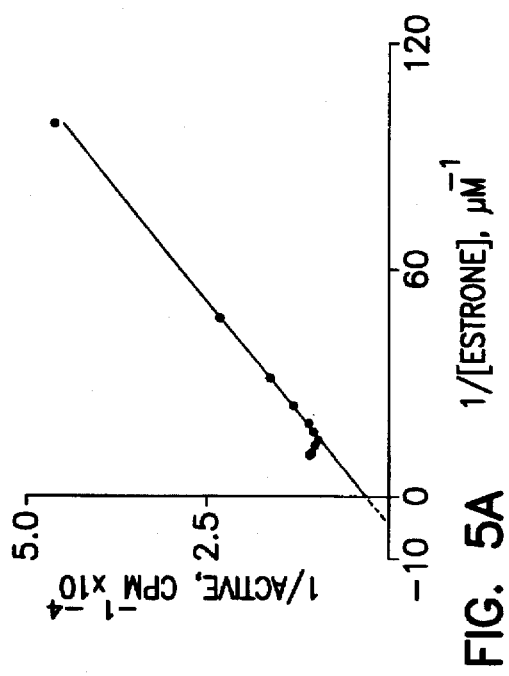
Figure 5D:
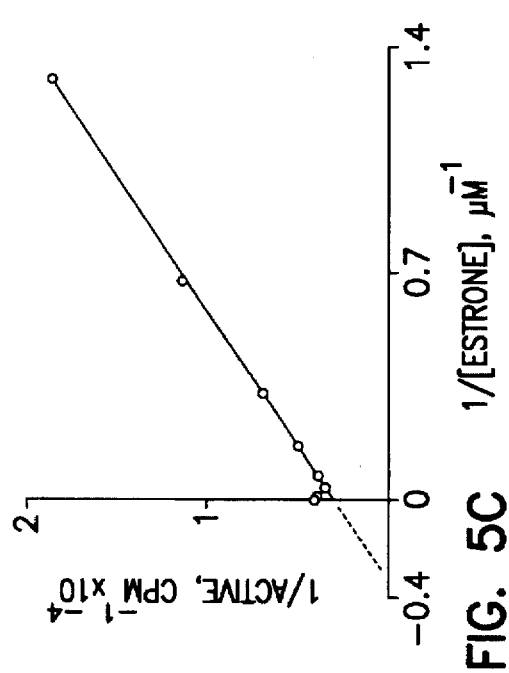

NaCl also has differential effects on ST enzyme activities in human liver (R. M. Weinshilboum et al., *Conjugation-Deconiugation Reactions in Drug Metabolism and Toxicity*, "Handbook of Experimental Pharmacology" series, R. C. Kauffman, Ed., Springer-Verlag (1994); I. A. Aksoy et al., *Drug Metab. Dispos.*, 21, 268–276 (1993)). The previously described EST and DHEA ST activity assays were used to measure ST activities of recombinant human liver EST enzyme and DHEA ST enzyme, respectively, wherein NaCl concentration in the reaction mixture was made 0.6 to 150 mM by the addition of 5 µL of a concentrated aqueous NaCl solution prior to incubation. EST activity of recombinant human liver EST enzyme (using its preferred substrate, estrone) transiently expressed in COS-1 cells was found to increase to 86% in the presence of 150 mM NaCl, while a peak activation of DHEA ST activity for human liver DHEA ST enzyme (using its preferred substrate, DHEA) of 62% occurred in the presence of 75 mM NaCl (FIG. 4C).

F. Northern and Southern blot analyses.

Northern blot analysis was performed with poly(A)$^+$ RNA isolated from eight different tissues using the ORF of human liver EST cDNA as a probe. Specifically, a human Multiple Tissue Northern (MTN) blot (Clontech, Palo Alto, Calif.) was probed with the EST cDNA coding region that had been radioactively labeled by random priming in the presence of

Figure 6:
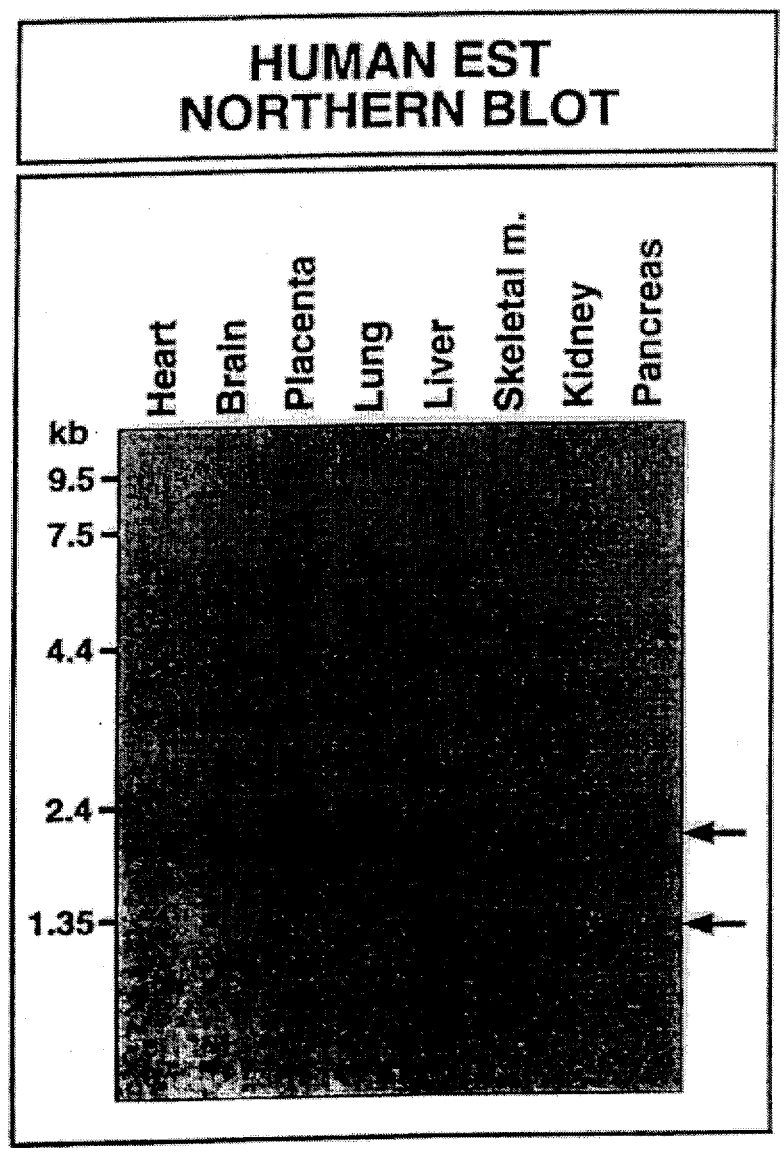
FIG. 6. Northern blot of human EST mRNA. A multiple tissue Northern blot was probed with the human liver EST cDNA open reading frame (ORF). Arrows indicate mRNAs detected in human liver and placenta.

[α-$^{32}$P]dCTP (A. P. Feinberg et al., *Anal. Biochem.*, 132, 6 (1983)). Hybridization was performed at 42° C. overnight in 5× SSPE, 50% freshly deionized formamide, 10× Denhardt's solution, 2% SDS and 100 μg/ml sonicated salmon sperm DNA. The blot was then washed at room temperature in 0.2× SSC and 0.1% SDS. Northern analysis showed the presence, in both liver and placenta, of a transcript approximately 2 kb in length (FIG. 6). Liver also showed a transcript approximately 1.2 kb in length and the possible existence of an even shorter mRNA species. The low intensity of the bands seen on Northern blot could help to explain the lack of success in screening cDNA libraries.

Figure 7:
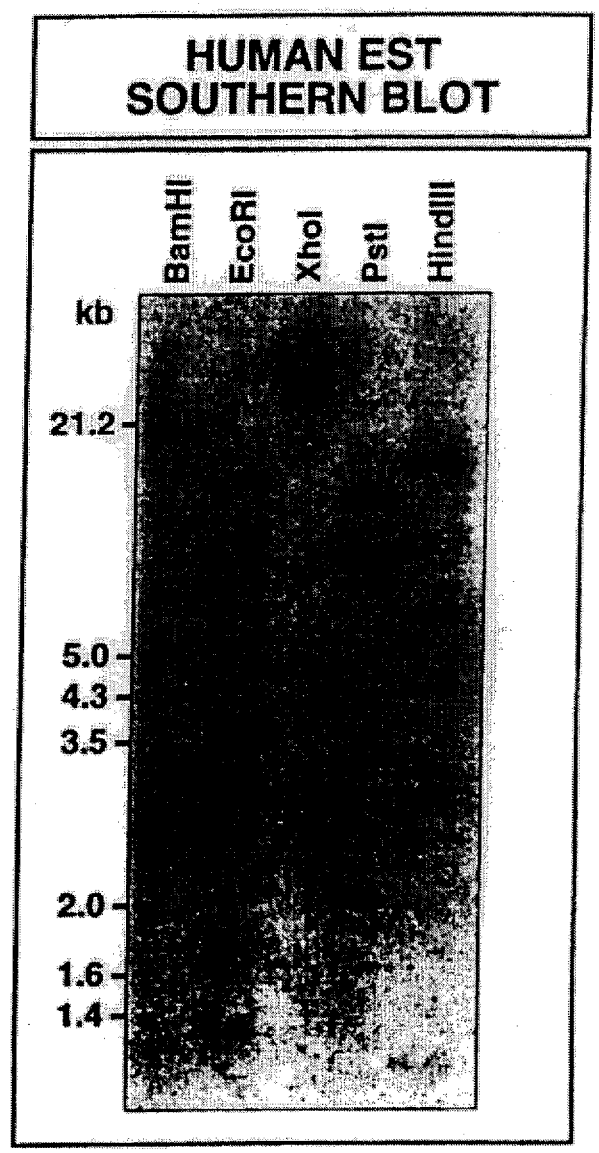
FIG. 7. Southern blot of human EST DNA. Five micrograms of human lymphocyte genomic DNA was exhaustively digested with restriction enzymes BamHI, EcoRI, XhoI, PstI and HindIII; separated by electrophoresis on a 0.8% agarose gel; transferred to an MSI nylon membrane and probed with the human liver EST cDNA ORF.

Southern blot analysis of human lymphocyte DNA was performed with the same probe in order to determine restriction fragment patterns (FIG. 7). Specifically, aliquots of 5 μg of human lymphocyte genomic DNA (Promega, Madison, Wis.) were digested with excess amounts of BamHI, EcoRI, XhoI, PstI, and HindIII, electrophoresed in a 0.8% agarose gel, and transferred to an MSI nylon membrane. Hybridization was performed overnight in 5× SSPE, 50% formamide, 10× Denhardt's solution, 100 μg/ml sonicated salmon sperm DNA, 0.5% SDS, and 10% dextran sulfate at 42° C. The membrane was washed twice in 2× SSPE and 0.2% SDS at room temperature, and twice in 0.1× SSPE and 0.2% SDS at 45° C. The size and number of DNA fragments hybridizing with the probe suggested that the number of EST or closely related genes in the human genome is small; only one or very few copies of the gene(s) for human liver EST appeared to be present in the human genome.

It will be appreciated by those skilled in the art that various modifications can be made to the above described embodiments of the invention without departing from the essential nature thereof. The invention is intended to encompass all such modifications within the scope of the appended claims. All publications, patents, and patent documents are incorporated by reference herein, as though individually incorporated by reference.

What is claimed is:

1. A cell line, the genome of which has been augmented by a chromosomally integrated DNA segment having a nucleotide sequence that encodes a human estrogen sulfotransferase having the amino acid sequence of SEQ ID NO:2 or a biologically active fragment of said human estrogen sulfotransferase.

2. The cell line of claim 1 wherein the DNA segment encodes a human estrogen sulfotransferase having the amino acid sequence of SEQ ID NO:2.

3. The cell line of claim 2 wherein the DNA segment has the nucleotide sequence of SEQ ID NO:1.

4. The cell line of claim 1 wherein the DNA segment encodes a biologically active fragment of a human estrogen sulfotransferase, wherein the human estrogen sulfotransferase has the amino acid sequence of SEQ ID NO:2.

5. A vector comprising a DNA segment having a nucleotide sequence that encodes a human estrogen sulfotransferase having the amino acid sequence of SEQ ID NO:2 or a biologically active fragment of said human estrogen sulfotransferase.

6. The vector of claim 5 wherein the DNA segment encodes a human estrogen sulfotransferase having the amino acid sequence of SEQ ID NO:2.

7. The vector of claim 6 wherein the DNA segment has the nucleotide sequence of SEQ ID NO:1.

8. The vector of claim 5 wherein the DNA segment encodes a biologically active fragment of a human estrogen sulfotransferase, wherein the human estrogen sulfotransferase has the amino acid sequence of SEQ ID NO:2.

* * * * *

UNITED STATES PATENT AND TRADEMARK OFFICE
CERTIFICATE OF CORRECTION

| | | |
|---|---|---|
| PATENT NO. | : 5,744,355 | Page 1 of 1 |
| APPLICATION NO. | : 08/437795 | |
| DATED | : April 28, 1998 | |
| INVENTOR(S) | : Weinshilboum et al. | |

It is certified that error appears in the above-identified patent and that said Letters Patent is hereby corrected as shown below:

In column 1, line 9, above "BACKGROUND OF THE INVENTION" insert

-- This invention was made with government support under GM028157 and GM035720 awarded by National Institutes of Health. The government has certain rights in the invention. --.

Signed and Sealed this

Twenty-fifth Day of December, 2007

JON W. DUDAS
*Director of the United States Patent and Trademark Office*

SEQUENCE LISTING ( 1 ) GENERAL INFORMATION:

( i i i ) NUMBER OF SEQUENCES: 19

( 2 ) INFORMATION FOR SEQ ID NO:1:

( i ) SEQUENCE CHARACTERISTICS:
( A ) LENGTH: 1063 base pairs
( B ) TYPE: nucleic acid
( C ) STRANDEDNESS: single
( D ) TOPOLOGY: linear ( i i ) MOLECULE TYPE: DNA ( i x ) FEATURE:
( A ) NAME/KEY: CDS
( B ) LOCATION: 107..989

( x i ) SEQUENCE DESCRIPTION: SEQ ID NO:1:

```
AGAAGTGGTT  CTCATCTTTT  TTTGCAGCTT  AAGATCTGCC  TTGGTATTTG  AAGAGATATA          60

AACTAGATCA  ATTTCTTTCA  CAGGATCAAC  TAAACAGTGT  ACCACA ATG AAT TCT            115
                                                       Met Asn Ser
                                                        1

GAA CTT GAC TAT TAT GAA AAG TTT GAA GAA GTC CAT GGG ATT CTA ATG              163
Glu Leu Asp Tyr Tyr Glu Lys Phe Glu Glu Val His Gly Ile Leu Met
         5                  10                  15

TAT AAA GAT TTT GTC AAA TAT TGG GAT AAT GTG GAA GCG TTC CAG GCA              211
Tyr Lys Asp Phe Val Lys Tyr Trp Asp Asn Val Glu Ala Phe Gln Ala
 20                  25                  30                  35

AGA CCA GAT GAT CTT GTC ATT GCC ACC TAC CCT AAA TCT GGT ACA ACC              259
Arg Pro Asp Asp Leu Val Ile Ala Thr Tyr Pro Lys Ser Gly Thr Thr
                     40                  45                  50

TGG GTT AGT GAA ATT GTG TAT ATG ATC TAT AAA GAG GGT GAT GTG GAA              307
Trp Val Ser Glu Ile Val Tyr Met Ile Tyr Lys Glu Gly Asp Val Glu
                 55                  60                  65

AAG TGC AAA GAA GAT GTA ATT TTT AAT CGA ATA CCT TTC CTG GAA TGC              355
Lys Cys Lys Glu Asp Val Ile Phe Asn Arg Ile Pro Phe Leu Glu Cys
             70                  75                  80

AGA AAA GAA AAC CTC ATG AAT GGA GTA AAA CAA TTA GAT GAG ATG AAT              403
Arg Lys Glu Asn Leu Met Asn Gly Val Lys Gln Leu Asp Glu Met Asn
         85                  90                  95

TCT CCT AGA ATT GTG AAG ACT CAT TTG CCA CCT GAA CTT CTT CCT GCC              451
Ser Pro Arg Ile Val Lys Thr His Leu Pro Pro Glu Leu Leu Pro Ala
```

| | | | | | | | | | | | | | | | | |
|---|---|---|---|---|---|---|---|---|---|---|---|---|---|---|---|---|
|100| | | | |105| | | | |110| | | | |115| |
|TCA|TTT|TGG|GAA|AAG|GAT|TGT|AAG|ATA|ATC|TAT|CTT|TGC|CGG|AAT|GCA|499|
|Ser|Phe|Trp|Glu|Lys 120|Asp|Cys|Lys|Ile|Ile 125|Tyr|Leu|Cys|Arg|Asn 130|Ala| |
|AAG|GAT|GTG|GCT|GTT|TCC|TTT|TAT|TAT|TTC|TTT|CTA|ATG|GTG|GCT|GGT|547|
|Lys|Asp|Val|Ala 135|Val|Ser|Phe|Tyr|Tyr 140|Phe|Phe|Leu|Met|Val 145|Ala|Gly| |
|CAT|CCA|AAT|CCT|GGA|TCC|TTT|CCA|GAG|TTT|GTG|GAG|AAA|TTC|ATG|CAA|595|
|His|Pro|Asn 150|Pro|Gly|Ser|Phe|Pro 155|Glu|Phe|Val|Glu|Lys 160|Phe|Met|Gln| |
|GGA|CAG|GTT|CCT|TAT|GGT|TCC|TGG|TAT|AAA|CAT|GTA|AAA|TCT|TGG|TGG|643|
|Gly|Gln|Val|Pro|Tyr 170|Gly|Ser|Trp|Tyr|Lys|His 175|Val|Lys|Ser|Trp|Trp| |
| |165| | | | | | | | | | | | | | | |
|GAA|AAG|GGA|AAG|AGT|CCA|CGT|GTA|CTA|TTT|CTT|TTC|TAC|GAA|GAC|CTG|691|
|Glu|Lys|Gly|Lys|Ser 185|Pro|Arg|Val|Leu|Phe 190|Leu|Phe|Tyr|Glu|Asp|Leu 195| |
|180| | | | | | | | | | | | | | | | |
|AAA|GAG|GAT|ATC|AGA|AAA|GAG|GTG|ATA|AAA|TTG|ATA|CAT|TTC|CTG|GAA|739|
|Lys|Glu|Asp|Ile|Arg 200|Lys|Glu|Val|Ile|Lys 205|Leu|Ile|His|Phe|Leu 210|Glu| |
|AGG|AAG|CCA|TCA|GAG|GAG|CTT|GTG|GAC|AGG|ATT|ATA|CAT|CAT|ACT|TCG|787|
|Arg|Lys|Pro|Ser 215|Glu|Glu|Leu|Val|Asp 220|Arg|Ile|Ile|His|His 225|Thr|Ser| |
|TTC|CAA|GAG|ATG|AAG|AAC|AAT|CCA|TCC|ACA|AAT|TAC|ACA|ACA|CTG|CCA|835|
|Phe|Gln|Glu 230|Met|Lys|Asn|Asn|Pro 235|Ser|Thr|Asn|Tyr|Thr 240|Thr|Leu|Pro| |
|GAC|GAA|ATT|ATG|AAC|CAG|AAA|TTG|TCG|CCC|TTC|ATG|AGA|AAG|GGA|ATT|883|
|Asp|Glu|Ile|Met|Asn 250|Gln|Lys|Leu|Ser|Pro|Phe|Met|Arg|Lys|Gly|Ile| |
| |245| | | | | | | | |250| | | |255| | |
|ACA|GGA|GAC|TGG|AAA|AAT|CAC|TTT|ACA|GTA|GCC|CTG|AAT|GAA|AAA|TTT|931|
|Thr|Gly|Asp|Trp|Lys|Asn|His|Phe|Thr|Val|Ala|Leu|Asn|Glu|Lys|Phe| |
|260| | | |265| | | | |270| | | | |275| | |
|GAT|AAA|CAT|TAT|GAG|CAG|CAA|ATG|AAG|GAA|TCT|ACA|CTG|AAG|TTT|CGA|979|
|Asp|Lys|His|Tyr 280|Glu|Gln|Gln|Met|Lys 285|Glu|Ser|Thr|Leu|Lys 290|Phe|Arg| |
|ACT|GAG|ATC|T|AAGAAGGTCT|TTCTTTACTT|AACATATCTG|ATATTAAAGA| | | | | | | | |1029|
|Thr|Glu|Ile| | | | | | | | | | | | | | |

TTTCTTTTCA TTATTCAAAA AAAAAAAAAA AAAA      1063

( 2 ) INFORMATION FOR SEQ ID NO:2:

( i ) SEQUENCE CHARACTERISTICS:
      ( A ) LENGTH: 294 amino acids
      ( B ) TYPE: amino acid
      ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
|Met|Asn|Ser|Glu|Leu|Asp|Tyr|Tyr|Glu|Lys|Phe|Glu|Glu|Val|His|Gly|
|1| | | |5| | | | |10| | | | |15|
|Ile|Leu|Met|Tyr|Lys|Asp|Phe|Val|Lys|Tyr|Trp|Asp|Asn|Val|Glu|Ala|
| | | |20| | | |25| | | | |30| | | |
|Phe|Gln|Ala|Arg|Pro|Asp|Asp|Leu|Val|Ile|Ala|Thr|Tyr|Pro|Lys|Ser|
| | |35| | | | |40| | | | |45| | | |
|Gly|Thr|Thr|Trp|Val|Ser|Glu|Ile|Val|Tyr|Met|Ile|Tyr|Lys|Glu|Gly|
| |50| | | | |55| | | | |60| | | | |
|Asp|Val|Glu|Lys|Cys|Lys|Glu|Asp|Val|Ile|Phe|Asn|Arg|Ile|Pro|Phe|
|65| | | | |70| | | | |75| | | | |80| |
|Leu|Glu|Cys|Arg|Lys|Glu|Asn|Leu|Met|Asn|Gly|Val|Lys|Gln|Leu|Asp|
| | | | |85| | | | |90| | | | |95| |

```
Glu  Met  Asn  Ser  Pro  Arg  Ile  Val  Lys  Thr  His  Leu  Pro  Pro  Glu  Leu
               100                      105                      110

Leu  Pro  Ala  Ser  Phe  Trp  Glu  Lys  Asp  Cys  Lys  Ile  Ile  Tyr  Leu  Cys
               115                      120                      125

Arg  Asn  Ala  Lys  Asp  Val  Ala  Val  Ser  Phe  Tyr  Tyr  Phe  Phe  Leu  Met
          130                      135                      140

Val  Ala  Gly  His  Pro  Asn  Pro  Gly  Ser  Phe  Pro  Glu  Phe  Val  Glu  Lys
145                           150                      155                     160

Phe  Met  Gln  Gly  Gln  Val  Pro  Tyr  Gly  Ser  Trp  Tyr  Lys  His  Val  Lys
                    165                      170                      175

Ser  Trp  Trp  Glu  Lys  Gly  Lys  Ser  Pro  Arg  Val  Leu  Phe  Leu  Phe  Tyr
               180                      185                           190

Glu  Asp  Leu  Lys  Glu  Asp  Ile  Arg  Lys  Glu  Val  Ile  Lys  Leu  Ile  His
          195                      200                      205

Phe  Leu  Glu  Arg  Lys  Pro  Ser  Glu  Glu  Leu  Val  Asp  Arg  Ile  Ile  His
     210                      215                      220

His  Thr  Ser  Phe  Gln  Glu  Met  Lys  Asn  Asn  Pro  Ser  Thr  Asn  Tyr  Thr
225                           230                      235                     240

Thr  Leu  Pro  Asp  Glu  Ile  Met  Asn  Gln  Lys  Leu  Ser  Pro  Phe  Met  Arg
                    245                      250                      255

Lys  Gly  Ile  Thr  Gly  Asp  Trp  Lys  Asn  His  Phe  Thr  Val  Ala  Leu  Asn
                    260                      265                      270

Glu  Lys  Phe  Asp  Lys  His  Tyr  Glu  Gln  Gln  Met  Lys  Glu  Ser  Thr  Leu
               275                      280                      285

Lys  Phe  Arg  Thr  Glu  Ile
               290
```

( 2 ) INFORMATION FOR SEQ ID NO:3:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:3:

```
Pro  Xaa  Ser  Phe  Trp  Glu  Lys
1                   5
```

( 2 ) INFORMATION FOR SEQ ID NO:4:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:4:

```
His  Tyr  Glx  Gln  Gln  Met  Lys
1                   5
```

( 2 ) INFORMATION FOR SEQ ID NO:5:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear (  i i ) MOLECULE TYPE: DNA ( x i ) SEQUENCE DESCRIPTION: SEQ ID NO:5:

CCAG YMTCAT TTTGGGAAAA 20

( 2 ) INFORMATION FOR SEQ ID NO:6:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:6:

TTCATTTGCT GCTSRTAGTG 20

( 2 ) INFORMATION FOR SEQ ID NO:7:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:7:

CCTGTCCTTG CATGAATTTC TCCAC 25

( 2 ) INFORMATION FOR SEQ ID NO:8:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:8:

GATAGATTAT CTTACAA 17

( 2 ) INFORMATION FOR SEQ ID NO:9:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:9:

CACGAATTCA CTATCGATTC TGGAACCTTC AGAGG 35

( 2 ) INFORMATION FOR SEQ ID NO:10:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:10:

CTGGTTCGGC CCACCTCTGA AGGTTCCAGA ATCGATAG                                             38

( 2 ) INFORMATION FOR SEQ ID NO:11:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:11:

GGGAAAGAGT CCACGTGT                                                                   18

( 2 ) INFORMATION FOR SEQ ID NO:12:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:12:

CCATCAGAGG AGCTTGTGGA CAGG                                                            24

( 2 ) INFORMATION FOR SEQ ID NO:13:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:13:

AACTGGAAGA ATTCGCGGCC GCAGGAATTT TTTTTTTTTT TTTTT                                     45

( 2 ) INFORMATION FOR SEQ ID NO:14:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:14:

AGTCCAATTG CAGTGTACCA CAATGAATTC TG                                                   32

( 2 ) INFORMATION FOR SEQ ID NO:15:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:15:

GACTCAATTG CCTTCTTAGA TCTCAGTTCG AA                                                   32

( 2 ) INFORMATION FOR SEQ ID NO:16:

( i ) SEQUENCE CHARACTERISTICS:
   ( A ) LENGTH: 8 amino acids
   ( B ) TYPE: amino acid
   ( C ) STRANDEDNESS: single
   ( D ) TOPOLOGY: linear ( i i ) MOLECULE TYPE: protein ( x i ) SEQUENCE DESCRIPTION: SEQ ID NO:16:

Tyr Pro Lys Ser Gly Thr Xaa Trp
1               5

( 2 ) INFORMATION FOR SEQ ID NO:17:

( i ) SEQUENCE CHARACTERISTICS:
      ( A ) LENGTH: 13 amino acids
      ( B ) TYPE: amino acid
      ( C ) STRANDEDNESS: single
      ( D ) TOPOLOGY: linear ( i i ) MOLECULE TYPE: protein ( x i ) SEQUENCE DESCRIPTION: SEQ ID NO:17:

Arg Lys Gly Xaa Xaa Gly Asp Trp Lys Asn Xaa Phe Thr
1               5                   10

( 2 ) INFORMATION FOR SEQ ID NO:18:

( i ) SEQUENCE CHARACTERISTICS:
      ( A ) LENGTH: 18 base pairs
      ( B ) TYPE: nucleic acid
      ( C ) STRANDEDNESS: single
      ( D ) TOPOLOGY: linear ( i i ) MOLECULE TYPE: DNA ( x i ) SEQUENCE DESCRIPTION: SEQ ID NO:18:

GACAGTACAC CACTTGTG                                                  1 8

( 2 ) INFORMATION FOR SEQ ID NO:19:

( i ) SEQUENCE CHARACTERISTICS:
      ( A ) LENGTH: 18 base pairs
      ( B ) TYPE: nucleic acid
      ( C ) STRANDEDNESS: single
      ( D ) TOPOLOGY: linear ( i i ) MOLECULE TYPE: DNA ( x i ) SEQUENCE DESCRIPTION: SEQ ID NO:19:

CAGACACAAG GAATTGTC                                                  1 8